United States Patent
Lund et al.

(10) Patent No.: US 6,702,827 B1
(45) Date of Patent: Mar. 9, 2004

(54) SLING ADJUSTMENT AND TENSIONING ACCESSORY

(75) Inventors: Robert E. Lund, St. Michael, MN (US); Johann J. Neisz, Coon Rapids, MN (US); Brian P. Watschke, Eden Prairie, MN (US); John W. Westrum, Jr., Prior Lake, MN (US)

(73) Assignee: American Medical Systems, Minnetonka, MN (US)

( * ) Notice: Subject to any disclaimer, the term of this patent is extended or adjusted under 35 U.S.C. 154(b) by 0 days.

(21) Appl. No.: 09/968,239

(22) Filed: Oct. 1, 2001

Related U.S. Application Data

(60) Provisional application No. 60/238,771, filed on Oct. 6, 2000.

(51) Int. Cl.[7] .............................................. A61B 17/08
(52) U.S. Cl. ........................... 606/151; 600/29; 600/30; 600/37
(58) Field of Search ................................. 606/151, 159, 606/232; 600/29, 30, 175, 179, 149, 150, 37; 602/78; 24/68 CD, 71 ST, 196, 200, 136 K, 300, 129 A; 128/885, 898, 899

(56) References Cited

U.S. PATENT DOCUMENTS

| | | | | |
|---|---|---|---|---|
| 1,748,227 | A | * 2/1930 | Hyams | 606/157 |
| 3,866,611 | A | * 2/1975 | Baumrucker | 128/885 |
| 3,996,937 | A | * 12/1976 | Williams | 606/158 |
| 4,938,760 | A | 7/1990 | Burton et al. | |
| 4,969,892 | A | 11/1990 | Burton et al. | |

(List continued on next page.)

FOREIGN PATENT DOCUMENTS

| | | |
|---|---|---|
| EP | 0650703 A1 | 6/1994 |
| EP | 0643945 A2 | 7/1994 |
| EP | 0 894 474 A1 | 2/1999 |
| WO | 93/19678 | 10/1993 |
| WO | 99/52450 | 10/1999 |
| WO | 00/13601 | 3/2000 |
| WO | 01/39670 A1 | 6/2001 |
| WO | 01/56499 A1 | 8/2001 |

OTHER PUBLICATIONS

Blavis et al., Type III Stress Urinary Incontinence: Importance of Proper Diagnosis and Treatment, Surgical Forum Gynecology and Obstetrics, p. 473–475, (admitted prior art).

(List continued on next page.)

Primary Examiner—Julian W. Woo
(74) Attorney, Agent, or Firm—Oblon, Spivak, McClelland, Maier & Neustadt, P.C.

(57) ABSTRACT

An anatomical support adjustment and tension control article for use in applying a tensioning force to anatomical support material disposed therein. The tension control article preferably comprises a base member disposing a plurality of tensioning members extending therefrom. The tensioning members create a tortuous pathway thereby providing a tensioning force to anatomical support material positioned therebetween. Additionally, at least one of the plurality of tensioning members may be removed from the device to alter the supportive tension applied by the device. The anatomical support material may be disposed between the plurality of tensioning members in a number of ways, thereby resulting in varying amounts of supportive tension being applied by the device.

5 Claims, 22 Drawing Sheets

U.S. PATENT DOCUMENTS

| | | | |
|---|---|---|---|
| 5,013,292 A | | 5/1991 | Lemay |
| 5,112,344 A | | 5/1992 | Petros |
| 5,487,746 A | * | 1/1996 | Yu et al. .................... 606/151 |
| 5,562,689 A | | 10/1996 | Green et al. |
| 5,591,163 A | | 1/1997 | Thompson |
| 5,649,940 A | | 7/1997 | Hart et al. |
| 5,836,315 A | | 11/1998 | Benderev et al. |
| 5,842,478 A | | 12/1998 | Benderev et al. |
| 5,860,425 A | | 1/1999 | Benderev et al. |
| 5,888,188 A | * | 3/1999 | Srougi et al. ................ 600/30 |
| 5,899,909 A | | 5/1999 | Claren et al. |
| 5,934,283 A | * | 8/1999 | Willem et al. ............... 600/29 |
| 5,997,554 A | | 12/1999 | Thompson |
| 6,039,686 A | | 3/2000 | Kovac |
| 6,042,534 A | | 3/2000 | Gellman et al. |
| 6,045,572 A | | 4/2000 | Johnson et al. |
| 6,050,937 A | | 4/2000 | Benderev |
| 6,068,591 A | | 5/2000 | Bruckner et al. |
| 6,071,290 A | | 6/2000 | Compton |
| 6,106,545 A | | 8/2000 | Egan |
| 6,110,101 A | | 8/2000 | Tihon et al. |
| 6,117,067 A | | 9/2000 | Gil-Vernet |
| 6,128,844 A | * | 10/2000 | Stermer et al. .............. 24/196 |
| 6,245,082 B1 | | 6/2001 | Gellman et al. |
| 6,302,840 B1 | | 10/2001 | Benderev |
| 6,328,686 B1 | | 12/2001 | Kovac |
| 6,334,446 B1 | | 1/2002 | Beyar |
| 6,463,932 B1 | * | 10/2002 | Single et al. .............. 128/885 |
| 2002/0115906 A1 | | 8/2002 | Miller |
| 2002/0151909 A1 | | 10/2002 | Gellman et al. |
| 2002/0151910 A1 | | 10/2002 | Gellman et al. |
| 2002/0156487 A1 | | 10/2002 | Gellman et al. |
| 2002/0156488 A1 | | 10/2002 | Gellman et al. |
| 2002/0156489 A1 | | 10/2002 | Gellman et al. |

OTHER PUBLICATIONS

Blavis, Jerry, Commentary: Pubovagianl Sling Procedure, Experience with pubovaginal Slings, pp. 93–101, (admitted prior art).

Jeffcoate, T.N.A, The Results of the Aldridge Sling Operation for Stress Incontinence, Journal of Obstetrics and Gynaecology, p. 36–39, 1956.

McGuire, Edward J. et al., Experience With Pubovginal Slings for Urinary Incontinence at the University of Michigan, pp. 90–93, (admitted prior art).

Moir, J. Chassar, The Gauze–Hammock Operation, The Journal of Obstetrics and Gynaecology of the British Commonwealth, pp. 1–9, vol. 75, No. 1, (Jan. 1968).

Narik.G et al., A Simplified Sling Operation Suitable for Routine Use, American Journal Obstetrics & Gynecology, pp. 401–405, vol. 84 No. 3, (Aug. 1, 1962).

Sloan, W.R. et al., Stress Incontinence of Urine a Retrospective Study of The Complications and Late Results of Simple Suprapubic Suburethral Fascial Slings, Journal of Urology, pp. 533–536, vol. 110, (Nov. 1973).

Studdiford, William, Transplantation of Abdominal Fascia for the Relief of Urinary Stress Incontinence, American Journal of Obstetrics and Gynecology, pp. 764–775.

Vesica Sling Kits, Simplifying Sling Procedures, Boston Scientific Microvasive, 4 pages (1998).

Vesica Sling Kits, A New Approach to Bladder Neck Suspension, Boston Scientific Microvasive, 4 pages (1995).

Rackley et al., Tension–Free Vaginal Tape and Percutaneous Vaginal Tape Sling Procedures, Techniques in Urology, vol. 7, No. 2, p. 90–100 (2001).

Decter, R., Use of the Fascial Sling for Neurogenic Incontinence: Lessons Learned, The Journal of Urology, vol. 150, p. 683–686 (Aug. 1993).

Spencer et al., A Comparison of Endoscopic Suspension of the Vesical Neck with Suprapubic Vesicourethropexy for Treatment of Stress Urinary Incontinence, The Journal of Urology, vol. 137, p. 411–415 (Mar. 1987).

Webster et al., Voiding Dysfunction Following Cystourethropexy: Its Evaluation and Management, The Journal of Urology, vol. 144, p. 670–673 (Sep. 1990).

Araki et al., The Loop–Loosening Procedure for Urination Difficulties After Stamey Suspension of the Vesical Neck, The Journal of Urology, vol. 144, p. 319–323 (Aug. 1990).

McIndoe G.A.J. et al., The Aldridge Sling Procedure in the Treatment of Urinary Stress Incontinence, Aust. NZ J Obstes Gynaecol, p. 238–239 (1987).

Kersey, J., The Gauze Hammock Sling Operation in the Treatment of Stress Incontintence, British Journal of Obstetrics and Gynaecology, vol. 90, p. 945–949 (Oct. 1983).

Ridley, John H., Appraisal of the Goebell–Frangenheim–Stoeckel Sling Procedure, American Journal Obst & Gynec., Vol. 95 No. 5, p. 741–721 (Jul. 1, 1986).

Morgan, J.E., A Sling Operation, Using Marlex Polypropylene Mesh for Treatment of Recurrent Stress Incontintence, American Journal of Obst. & Gynec., vol. 106 No. 3, p. 369–377, (Feb. 15, 1970).

Stanton, Stuart L., Suprapubic Approaches for Stress Incontintence In Women, Journal of American Geriatrics Society, vol. 38, No. 3, p. 348–351 (Mar. 1990).

Raz, Female Urology, McGuire, Edward J. et al., Abdominal Fascial Slings, Slings, p. 369–375 (1996).

* cited by examiner

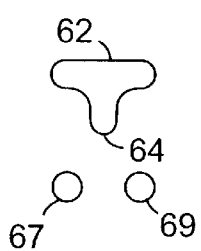 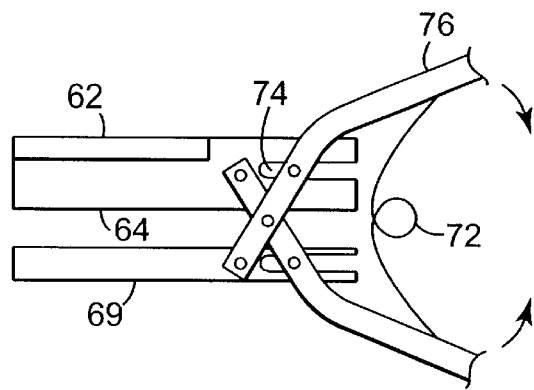
Fig. 10a    Fig. 10b
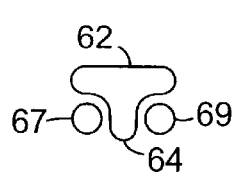 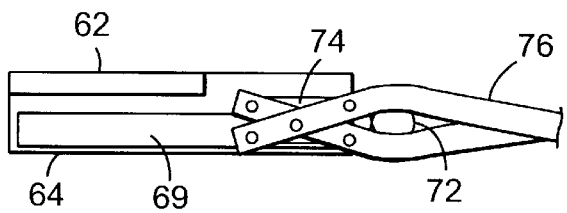
Fig. 10c    Fig. 10d

SLING ADJUSTMENT AND TENSIONING ACCESSORY

CROSS REFERENCE TO RELATED APPLICATIONS

The present application claims priority to U.S. Provisional Application Ser. No. 60/238,771, filed Oct. 6, 2000 (the entire contents of which are fully incorporated herein by reference).

BACKGROUND

Urinary incontinence, or the inability to control urination, is a major and debilitating problem affecting millions of people, especially women. The female's natural support system for the urethra is a hammock-like supportive layer composed of endopelvic fascia, the anterior vaginal wall, and a distal attachment to the pubic bone. Weakening and elongation of the pubourethral ligaments and the arcus tendineus fascia pelvis, weakening of the endopelvic fascia and pubourethral prolapse of the anterior vaginal wall are some common characteristics of a patient with urinary incontinence.

Many procedures have been devised to treat urinary incontinence. Some have the goal of elevating the neck of the bladder to return it to a higher retropubic position. Many pubovaginal sling procedures have been developed to treat urinary incontinence. Some of these procedures involve positioning anatomical sling material under the urethra to provide elevation and support of the urethra and/or the bladder neck. Examples of attachment sites for the sling include the anterior or superior portion of the pubis (e.g. with bone anchors and associated sutures), Cooper's ligament, or rectus abdominus fascia. Examples of procedures for treating incontinence are disclosed in U.S. Pat. Nos. 5,112,344; 5,611,515; 5,842,478; 5,860,425; 5,899,909; 6,039,686, 6,042,534 and 6,110,101.

Slings used for pubovaginal procedures differ in the type of implantable material and anchoring methods. In some cases, the sling is placed under the bladder neck and secured via suspension sutures to a point of attachment (e.g. bone) through an abdominal and/or vaginal incision.

Complications associated with procedures for treating incontinence include urinary retention, bladder instability and erosion of an implanted article into surrounding tissue. See Spencer et al, *A Comparison of Endoscopic Suspension of the Vesical Neck With Suprapubic Vesicourethropexy for Treatment of Stress Urinary Incontinence*, J. Urol. 137: 411, (1987); Araki et al, *The Loop Loosening Procedure for Urination Difficulties After Stamey Suspension of the Vesical Neck*, J. Urol., 144; (1990); and Webster et al., *Voiding Dysfunction Following Cystourethropexy: Its Evaluation and Management*, J. Urol., 144; (1990).

With respect to sling procedures, if the sling mesh is too loosely associated with its intended physiological environment, the mesh may be ineffective in supporting the urethra and treating incontinence. Several complications can arise from a mesh that is too tightly placed including retention, sling erosion and other damage to surrounding tissue such as the urethra and vagina.

The TVT Tension-free Vaginal Tape procedure utilizes a knitted Prolene™ nonabsorbable, polypropylene mesh. The mesh is a substantially flat, rectangular woven article. The mesh includes a plurality of holes that are sized to allow tissue ingrowth to help avoid infection. A removable plastic sheath surrounds the mesh and is used during insertion of the mesh. The sling is positioned near the urethra without the use of bone anchors. Once the sheath is removed from the mesh of the TVT product, friction between the mesh and tissue keeps the mesh in position and it becomes very difficult to subsequently adjust the position of the mesh relative to tissue. Attempts to move the sling once the sheath is removed may damage the sling or adjacent tissue such as the urethra or vagina.

Proper tension of a sling is an important factor for a successful surgical procedure. Surgical approaches to applying tension or slack in a sling procedure vary widely. See Decter, *Use of the Fascial Sling for Neurogenic Incontinence: Lessons Learned*, The Journal of Urology, Vol. 150, 683–686 (1993). While the TVT procedure suggests using a scissors or hemostat placed between the sling and urethra to set the looseness of the TVT mesh sling, a flat blunt surgical instrument is placed between the sling and urethra in other procedures. See Moir et al., *The Gauze-Hammock Operation*, The Journal of Obstetrics and Gynaecology of the British Commonwealth, Vol. 75, No. 1 (January 1968) Pps. 1–9.

The TVT sling procedure instructs users to place a scissors or hemostat between the urethra and the sling to ensure ample looseness of the sling. There are several problems associated with this approach. First, the type of scissors or hemostat used to tension the sling may differ in size, potentially causing application of different amounts of looseness for the sling. For example, one surgeon may use a Mayo scissors while another surgeon may use a hemostat or flat, blunt instrument. It is believed that the use of different instruments with different sizes inherently leads to inconsistency in the amount of slack or looseness provided in a sling. This inconsistency could lead to inconsistent therapeutic results, misleading medical data and other clinical errors. Second, even if the same surgical instrument is used, the precise portion of the surgical instrument used to set the looseness of the sling may vary along the length instrument. For example, some surgeons use the tips of closed Mayo scissors to tension a sling. Mayo scissors are curved and the precise thickness of a scissors along its length varies significantly. See FIG. 5 of Rackley et al., *Tension-free Vaginal Tape and Percutaneous Vaginal Tape Sling Procedures*, Techniques in Urology, Vol. 7, No. 2, pp. 90–100 (2001). Depending upon how far the Mayo scissors tips are inserted between the sling and the urethra, the actual amount of looseness provided can vary significantly.

Other prior art sling procedures use bone anchors or other methods of securing a sling. A difficulty that contributes to the unnatural positioning of the urethra is that some attachment sites, such as the rectus abdominus fascia or the top of the pubic bone, require very long sutures. Long sutures increase the difficulty in achieving the proper tension in the sutures and sling and increase the chances that intervening anatomical structures may interfere with proper tension. Improper sling tension or sling suture tension can result in increased lateral movement and momentum of the support structures or mesh sling when they are moved due to intra-abdominal pressures.

U.S. Pat. No. 5,863,315 discloses a method of tensioning a suspended tissue mass. The method utilizes a suture tensioner comprising a handle, a main body and an annular recess.

More than a year prior to the filing date of the present application, Vesica Sling Kits were sold (by Boston Scientific, Microvasive, USA) in the United States that included a Suture Spacer. Surgeons were instructed to place the Suture Spacer on the top of the pubic tubercle (which is a location remote from the sling and remote from the urethra, vagina and bladder neck). The surgeon then places a suture about the Suture Spacer and ties a knot. As a knot is tied, the Suture Spacer is pulled downward onto the top of the pubic bone. Six or seven additional throws are tied and the Suture Spacer is withdrawn.

U.S. Pat. No. 5,474,518 discloses a device for correcting urinary incontinence by use of vesical suspension. The device includes a box that houses a drum with a toothed wheel that engages a worm gear.

U.S. Pat. Nos. 4,938,760 and 4,969,892 disclose a method of suspending the urethrovesical junction in females. An anchoring means for anchoring a suture in tissue is disclosed. The anchoring means comprises a rotating spool, a driving gear and an adjusting means.

PCT International Pub. No. WO 01/39670 discloses an implantable support sheet for providing suburethral stabilization for female patients. A clip is disclosed that inhibits folding of a central part of the sheet about its longitudinal axis.

U.S. Pat. No. 6,106,545 discloses a suture tensioning and fixation device for attachment of tendon to muscle or reattachment of ligaments to bone. The device includes a retaining element and suture thread engaging portions.

U.S. Pat. No. 6,117,067 discloses a device for the height-adjustable fixing and support of internal organs. The device includes a sling, threads, tube, small capsule and chamber. A needle is used to introduce or extract liquid.

U.S. Pat. No. 6,068,591 discloses an apparatus for treatment of female stress urinary incontinence with a support harness. The patent discloses an adjustable setting and Carter pin.

BRIEF SUMMARY

The present invention is directed to an article useful in surgical procedures. The article assists surgeons in providing consistent, repeatable relationships between implantable materials such as slings, and target tissue such as urethra tissue. In use with a plurality of different surgeons and a plurality of different patients, the present invention can contribute to consistent, repeatable medical results, more reliable medical data and improved medical decisions.

The article comprises a portion adapted to be grasped, and at least one tensioning member that is sized and shaped to afford predetermined looseness of an anatomical support material, such as a sling, relative to anatomical tissue, such as a urethra.

A variety of procedures are contemplated, including, for example, pubovaginal sling procedures. The present invention is particularly suitable for use in a sling procedure that places a sling in a therapeutically effective position. Preferably, the sling is placed to control the pressure applied to the urethra to obtain or restore normal anatomy and continence.

In a preferred embodiment, the article comprises a plurality of tensioning members. In one embodiment the article includes movement means for moving at least one tensioning member between an open position for receiving the anatomical support material and a closed position that associates the article with the anatomical support material. Preferably, the movement means comprises means for affording substantial parallel movement between tensioning members to resist wrinkling of the anatomical support material.

In another preferred embodiment, the plurality of tensioning members are arranged to afford a plurality of tortuous paths of different lengths, and the anatomical support material may be associated with the article along one of the tortuous paths.

In another embodiment, the article includes means for moving at least one of the tensioning members relative to another tensioning member to change the length of a tortuous path.

In another aspect, the present invention comprises a device for applying tension to a surgical sling.

In another aspect, the invention comprises a tensioning device comprises a base member having a plurality of tensioning members extending outwardly from the base member, thereby creating a tortuous pathway for sling material positioned thereon. When the sling material is used in a pubovaginal sling procedure, the tensioning device provides additional tensioning support to the urethral body, the bladder neck, or both.

The tensioning device of the present invention may have a number of different configurations. For example, in one embodiment, the base member is arcuate. In an alternate embodiment, the base member is rectangular. Additionally, the base member may include a directional indicator to aid the user in applying the device. In yet another embodiment, the base member may include an integral or detachable grasping member. The base member may further include at least one sling material locking member having an open position which allows removal of the sling material from the device, and a closed position to the retain sling material within the device.

The tensioning members of the present invention may comprise a plurality of configurations, including circular members, oval members, or other shaped members capable of retaining material disposed therein. Similarly, the tensioning members may be manufactured from a plurality of materials including, without limitation, silicone elastomer, acetate, acetal polyurethane, acrylic, elastomer, stainless steel, polysulfone, nylon, polycarbonate, polyethermide, acetal, ABS, bioresorbable materials or other biologically-compatible materials for temporary or permanent implantation.

In another form, the device remains implanted and can be adjusted in the subsequent post operative period by removing all or some of the tensioning members or by constructing the tensioning members of a bioresorbable material.

Additionally, the tensioning members may be constructed so that they indicate the preload on the sling through a deflection or alignment of the tensioning members.

The present invention may further include various methods of using the tensioning device for creating and using a tortuous pathway to apply tensioning force to a material disposed therein.

In another aspect, the present invention comprises a method of providing a uniform distance between the urethra and a sling comprising: providing a sling and tensioning article, associating the tensioning article with the sling, implanting the sling and associated tensioning article in a position substantially adjacent or, alternatively, just touching the urethra, and then removing the tensioning article. Optionally, the step of providing a sling and tensioning article includes the step of providing an insertion sheath surrounding the sling; and the step of associating the tensioning article with the sling includes the step of associating the sling and sheath combination with the tensioning article.

In another aspect, the present invention comprises a method of treating incontinence comprising the steps of: (i)

providing a support material with at least a portion that is elastically deformable, (ii) elastically deforming at least a portion of the support material to tension the support material; (iii) providing a tensioning article, (iv) applying the tensioning article to the tensioned support material to retain at least a portion of the support material in an elastically deformed condition; (v) implanting the support material with applied tensioning article in a patient; removing the tensioning article to increase the tension provided by the support material.

In another method, the present invention comprises a method of reducing the looseness of an implanted sling comprising the steps of: providing a tensioning article, and associating the tensioning article with the sling in vivo to tighten the sling.

In another method, the tensioning member remains implanted and provides an elastic stress relieving component to the sling in the immediate or long term post operative period. This is particularly useful when the sling is made of an elastic material such as a silicone elastomer.

In another aspect, the present invention comprises a kit for treating incontinence. The kit comprises surgical articles for implanting a surgical sling, and a tensioning article.

Other features and advantages of the present invention will become apparent from a consideration of the following detailed description.

BRIEF DESCRIPTION OF THE DRAWINGS

Other features and advantages of the present invention will be seen as the following description of particular embodiments progresses in conjunction with the drawings, in which:

FIGS. 8a–8d are views of an alternative embodiment of the present invention wherein:

FIG. 8a shows an end view of an alternative embodiment of tensioning device shown in a closed position;

FIG. 8b shows a side view of the device of FIG. 8a;

FIG. 8c is an end view of the device of FIG. 8a shown in an open position;

FIG. 8d is a side view of the device of FIG. 8c;

FIGS. 9a–9d are views of an alternative embodiment of the present invention wherein:

FIG. 9a shows an end view of an alternative embodiment of tensioning device shown in a closed position;

FIG. 9b shows a side view of the device of FIG. 9a;

FIG. 9c is an end view of the device of FIG. 9a shown in an open position;

FIG. 9d is a side view of the device of FIG. 9c;

FIGS. 10a–10d are views of an alternative embodiment of the present invention wherein:

FIG. 10a shows an end view of an alternative embodiment of tensioning device shown in an open position;

FIG. 10b shows a side view of the device of FIG. 10a;

FIG. 10c is an end view of the device of FIG. 10a shown in a closed position;

FIG. 10d is a side view of the device of FIG. 10c;

FIG. 18b is a side view of another embodiment of tensioning device according to the present invention shown in an open position;

DETAILED DESCRIPTION

Figure 1:
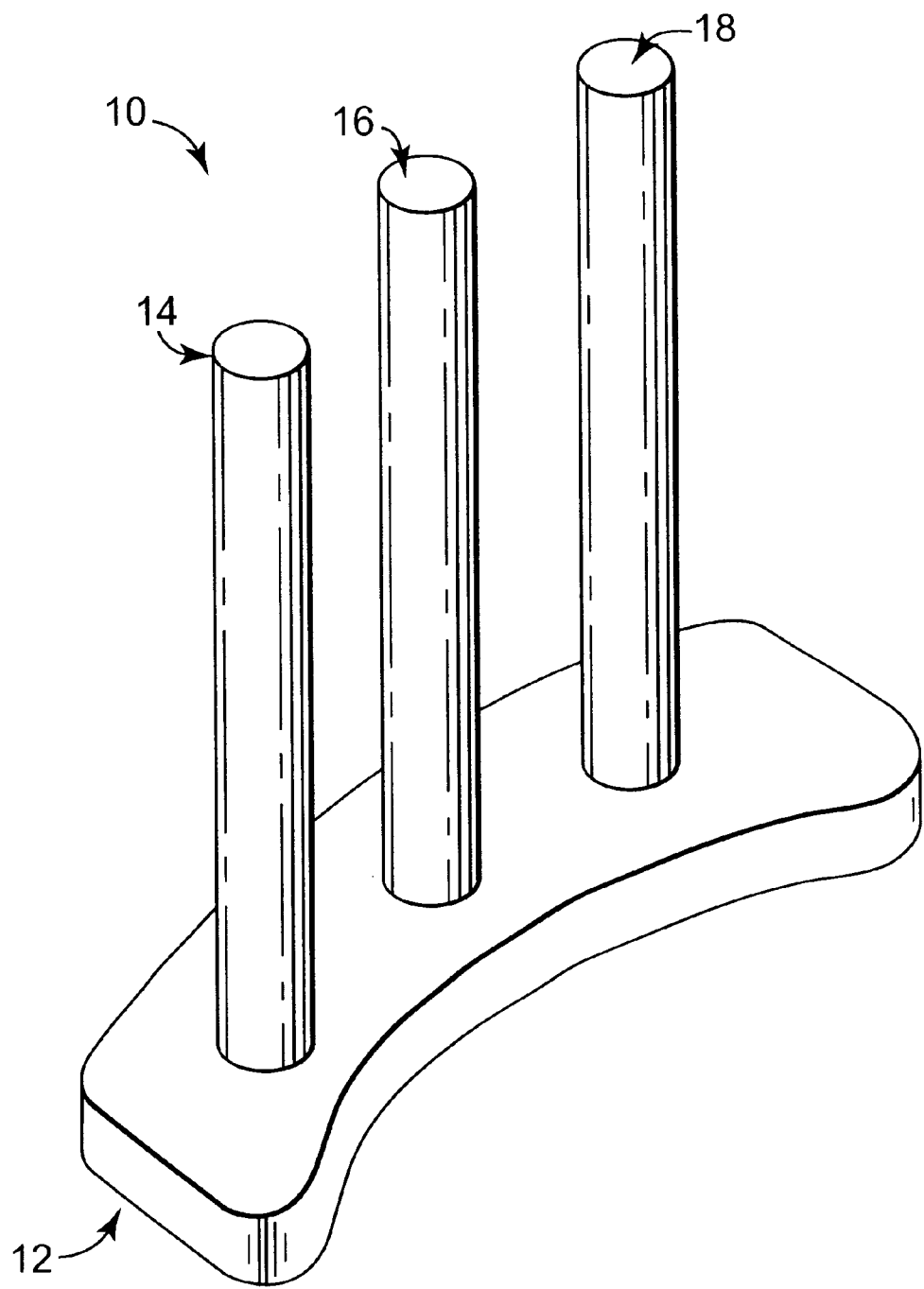
FIG. 1 shows a perspective view of an embodiment of tensioning device of the present invention.

The present invention comprises an article, preferably a tension control article, for use in conjunction with an implantable article such as a sling. In a preferred embodiment, the tension control article is utilized in conjunction with a sling for treating urinary incontinence. The tension control article may be used in conjunction with a wide variety of slings and other surgical procedures. For example, the present invention may be utilized in conjunction with the slings and procedures described in U.S. Pat. Nos. 5,520,700; 5,611,515; 5,842,478; 5,860,425; 5,972,000; 6,039,686, 6,042,534 and 6,110,101 (the entire contents of which are herein incorporated by reference in their entirety) and U.S. patent application Ser. No. 09/917,562 (entitled: Implantable Article and Method) and Ser. No. 09/917,443 (entitled: Sling Delivery System and Method of Use); and Ser. No. 09/917,445 (entitled: Surgical Instrument and Method); both filed Jul. 27, 2001 (the entire contents of each of which are herein incorporated by reference. Commercial examples of slings, instructions for use and kits that may be modified to incorporate the present invention include the In-Fast Sling System and the SPARC Sling System available from American Medical Systems of Minnetonka, Minn., and the transvaginal TVT Sling System available from Ethicon (a division of Johnson & Johnson).

Preferably, the tension control article is associated with an implantable material (e.g. a sling). Suitable implantable materials associated with the present invention include synthetic and non-synthetic materials. Suitable non-synthetic implantable materials include human fascia lata, treated animal (e.g. bovine or porcine or equine pericardium) tissue, autologous tissue, cadaver tissue, homografts, xenografts, heterografts, allografts and combinations of such materials. Suitable synthetic materials include knitted polypropylene slings alone, such slings with surrounding sheaths, or silicone coated polymer slings, such as those described in U.S. patent application Ser. No. 09/939,098 (entitled Coated Sling Material), filed Aug. 4, 2001 (the entire contents of which are herein incorporated by reference). Alternatively, the tension control article may be associated with sutures associated with slings. Such sutures typically extend from an implanted bone anchor on the pubic bone, or from the rectus abdominus fascia. These sutures hold the sling in place in the body.

The present invention may also be used in conjunction with surgical procedures other than those designed to strictly address incontinence. For example, the present invention may be used in conjunction with a sacral colpopexy procedure designed to treat vaginal prolapse.

The tension control article of the present invention, when used with transvaginal or suprapubic surgical anatomical support material (e.g. a sling) or sutures, is designed to provide an adjustable tensioning or spacing mechanism as an objective aid for surgeons in associating the sling or suture with a therapeutically effective position. The article of the present invention assists surgeons in consistently and repeatably associating a sling with its intended physiological environment (e.g. the bladder neck or urethra, or both).

The tension control article is preferably positioned on a portion of anatomical support material. In one embodiment, the tension control article has a plurality of tensioning members that are sized and shaped to provide a tortuous pathway for the sling material. When the tension control article is associated with the sling material and the sling material is placed at its intended anatomical location, the tension control article results in an increase in the supportive tension that is applied by the sling to anatomical structures relative to that supportive tension that would be applied to the anatomical structures in the absence of the tension control article.

In one embodiment, the size and shape of the tensioning members are selected to provide a predetermined slack in the sling material once the article is removed from the sling material. For example, for a tension free surgical sling procedure for treating incontinence, the tension control article may be associated with the sling and the sling/tension control article combination may be implanted to just touch the urethra of a patient. In this example, once this penultimate orientation of the sling and urethra is achieved, the tension control article may then be removed to ensure a consistent, uniform amount of slack is provided between the sling and the urethra. Providing a uniform, consistent, repeatable amount of looseness in each surgical procedure reduces the chances that patient data is corrupted by the vagaries associated with a particular surgeon's preferences or lack of training or experience. As a result, it is believed that the present invention can lead to more consistent medical results.

The tension control article of the present invention may be constructed of a wide variety of materials. Suitable materials include those that may be permanently implanted in the body, temporarily implanted, and/or completely removed prior to the end of the surgical procedure. The material used to construct the tension control article should be biocompatible and may comprise bioresorbable materials or permanent, biocompatible materials or combinations thereof.

FIG. 1 shows an embodiment of the anatomical support adjustment and tension control article 10 for use with suspension sutures, surgical slings, or other anatomical supports. In this embodiment, the present invention includes a base member 12 and three tensioning members 14, 16, and 18 attached thereto. Optionally, more than three tensioning members may be positioned on the base member. The base member 12 is preferably arcuate and includes beveled edges to reduce or eliminate damage to the surrounding tissue and anatomical support material disposed thereon. In an alternate embodiment, the body member 12 may form any other configuration which facilitates support of the urethra and which minimizes damage to the surrounding tissue and anatomical structures. The device 10 may be manufactured in a plurality of sizes to accommodate the physiological or anatomical constraints of the patient and the location of use. The configuration of the device 10 enables a user to adjust the length of anatomical support material positioned therein and adjustably control the supportive tension applied to tissue.

The device 10 may be constructed of a plurality of materials, including, for example, titanium, stainless steel, nylon, polycarbonate, polysulfone, ABS, ultem, polyetherimide, and polyacetate or combinations thereof, thereby providing a relatively rigid device. In an alternate embodiment of the present invention, the device 10 may be manufactured from moderately flexible materials, such as acetal, or soft flexible materials, such as silicon elastomer or polyurethane, should a more flexible support mechanism be desired. In yet another embodiment, the device 10 may be manufactured from biodegradable materials or polymers.

The device 10 may further include or be manufactured from materials having distinct radio opacities or echogenic properties, thereby enabling location of the device 10 in post-surgical procedures. In yet another embodiment, the present invention may be manufactured from materials having distinct optical properties, wherein the application of force to device 10 alters the visual appearance of, or light transmission through, the device 10. Furthermore, it is considered within the scope of the claimed invention to construct the device 10 from multiple materials. For example, the device 10 may comprise a base member 12 constructed of polyacetate, or a similar rigid material, and the tensioning members 14, 16, and 18, respectively, constructed of a flexible material. Other biocompatible materials and material combinations not specifically listed herein, may also be used to fabricate the device 10 and are included within the scope of the claimed invention.

The members 14, 16 and 18 may be integrally molded with the base portion. Alternatively, they could be releasably attached to the base portion to afford adjustment of the sling. For example, the members 14, 16 and 18 may be constructed to be separable from the base portion by use of a remotely actuated device (e.g. a device that utilizes electromagnetic energy). In particular, a magnetic attachment of one or more of the members 14, 16 and 18 and the base portion 12 may be provided. This magnetic attachment may be eliminated by a remotely activated device. This embodiment affords adjustment in the tension of a sling post operatively without requiring a subsequent incision.

Figure 2A:
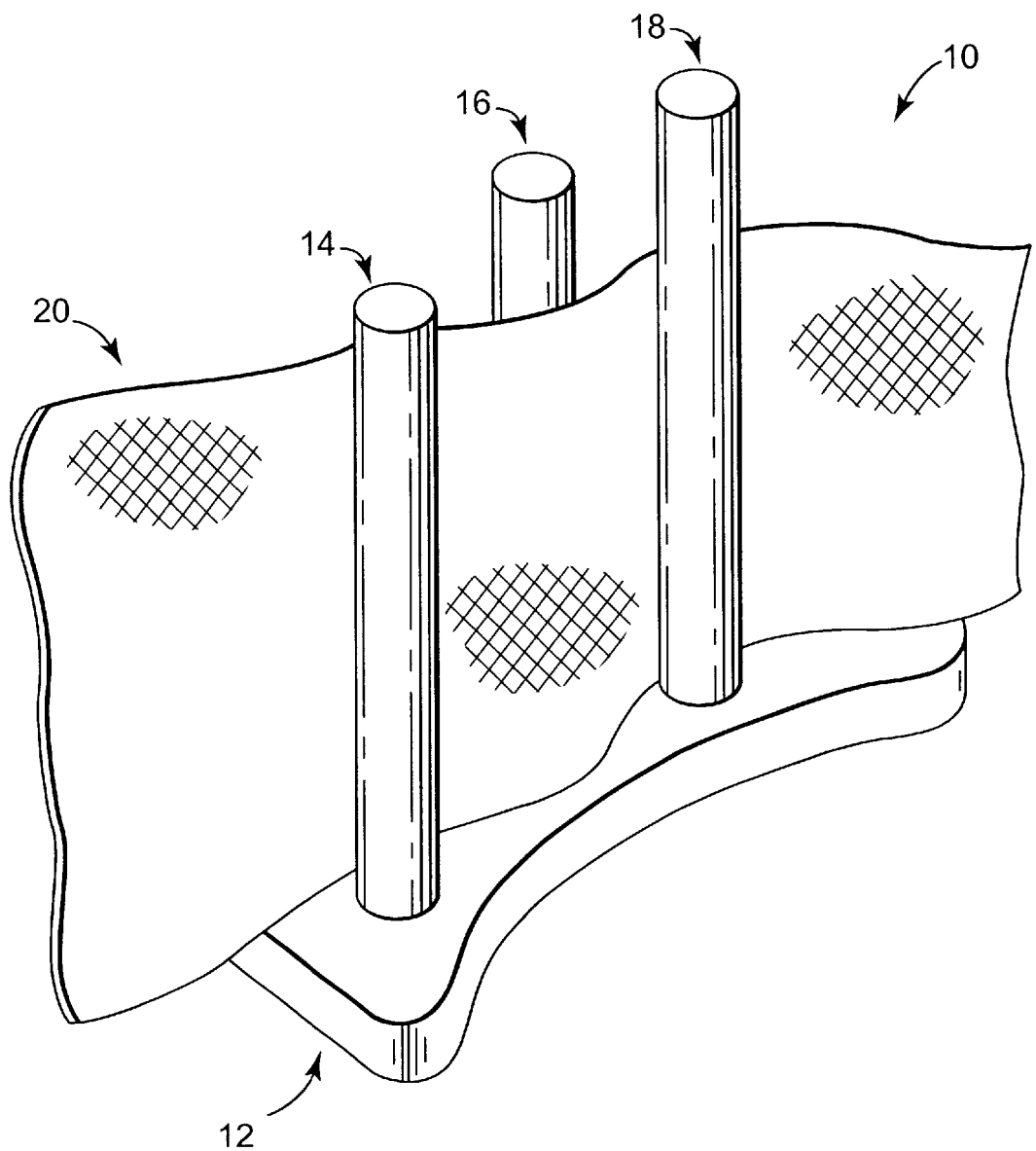
FIG. 2a is a perspective view of the tensioning device of FIG. 1 engaging sling material positioned thereon.
Figure 2B:
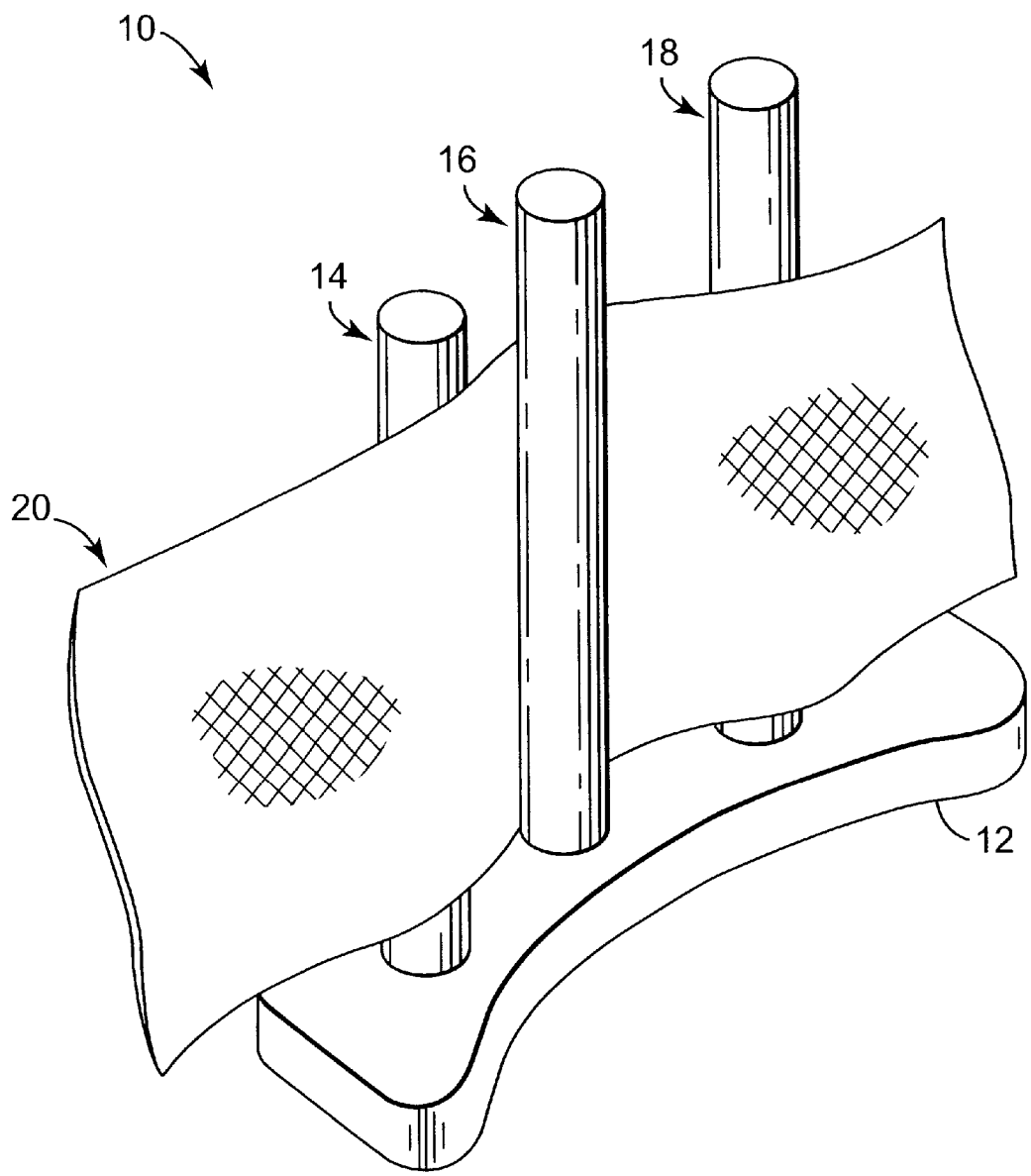
FIG. 2b is a perspective view of an alternate embodiment of the tensioning device of the present invention engaging sling material positioned therein.

FIGS. 2a and 2b show alternative methods of positioning the present invention on a portion of anatomical support material. FIG. 2a shows one method of using the tensioning device 10 to engage a portion of anatomical support material 20, wherein the material 20 is positioned within a tortuous pathway formed by the plurality of tensioning members 14, 16, and 18 respectively. FIG. 2b shows an another method of using the tensioning device 10, wherein the anatomical support material 20 traverses an alternate tortuous pathway formed by the plurality of tensioning members 14, 16, and 18.

Generally, the longer the tortuous path, the greater the slack provided in the sling 20 once the tension control article 10 is removed. Also, the longer the tortuous path, the more slack is taken up in a sling 20 once the tension control article 10 is associated with the sling. For the same clip 10, the length of the tortuous path in FIG. 2a is different than the length of the tortuous path in FIG. 2b. As a result, the same tension control article may be utilized to provide a plurality of different slacks in the anatomical support material (e.g. sling) 20.

Figure 3:
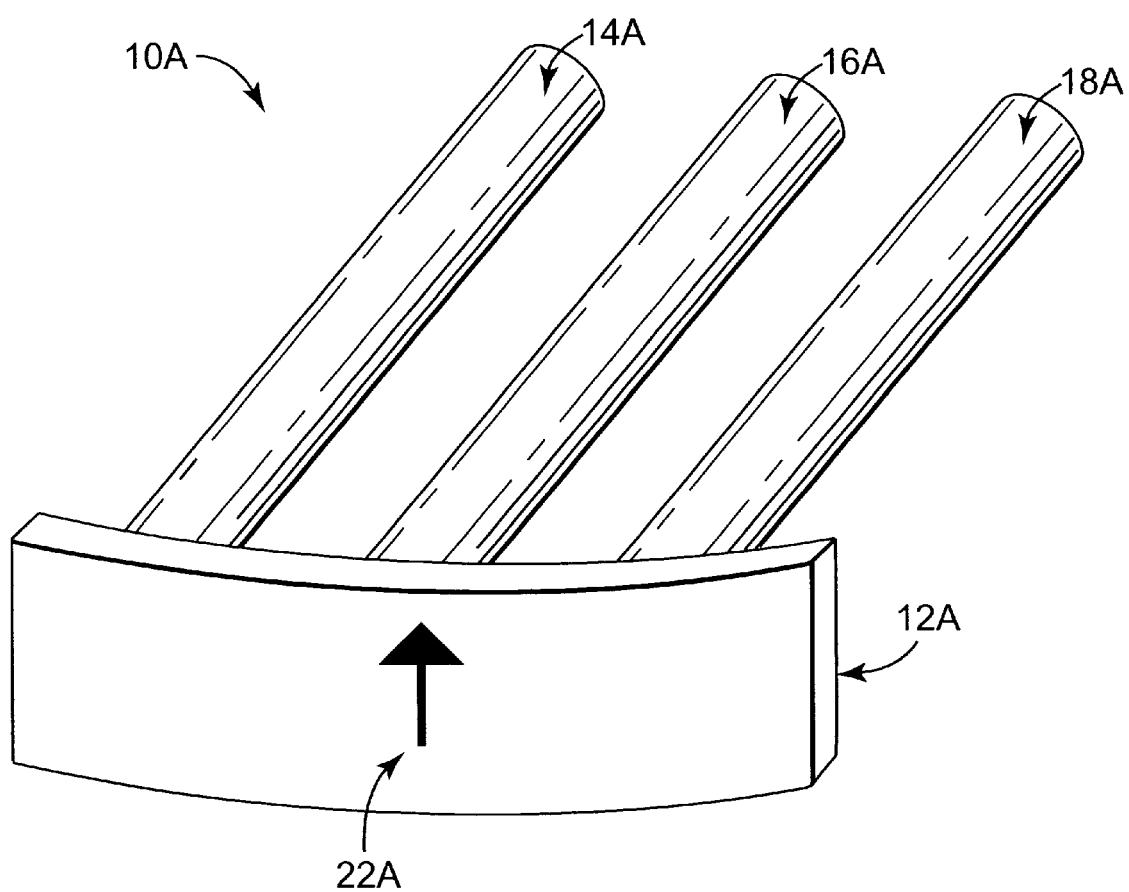
FIG. 3 shows a perspective view of an embodiment of tensioning device of the present invention having an orientation indicator positioned thereon.

A second embodiment of tension control article 10A is illustrated in FIG. 3. The tension control article 10A has tensioning members 14A, 16A and 18A, and base member 12A. The tension control article 10A further comprises a directional indicator 22A included on the body member 12A. The directional indicator 22A assists the user in properly applying the device 10A to a portion of anatomical support material. As shown in FIG. 3, the directional indicator 22A may comprise an arrow printed on, embossed or integrally disposed on a surface of the base member 12A. Alternatively, the directional indicator may include figures, shapes, letters, or other markings formed, printed, or otherwise included on the device 10A. In another embodiment, the base member 12A may include a tension scale, enabling the user to determine the amount of load imposed on the tensioning members. Alternatively, displacement of flexible members may be used to indicate the applied load. For example, deflection or alignment of the tensioning members may be used to indicate the relative preload on the sling 20.

Figure 4A:
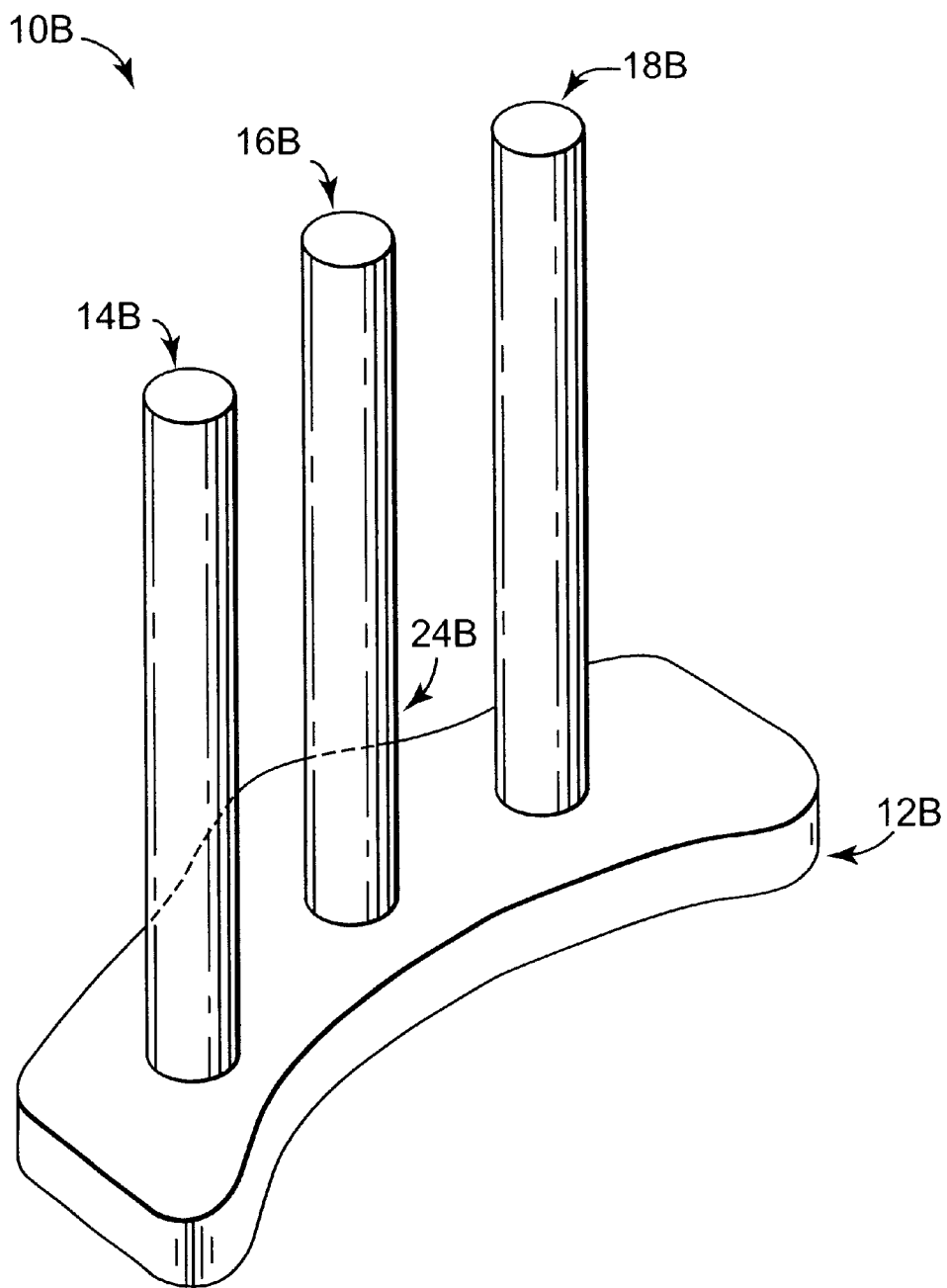
FIG. 4a shows a perspective view of another embodiment of tensioning device of the present invention having a grasping structure disposed on the base member.
Figure 4B:
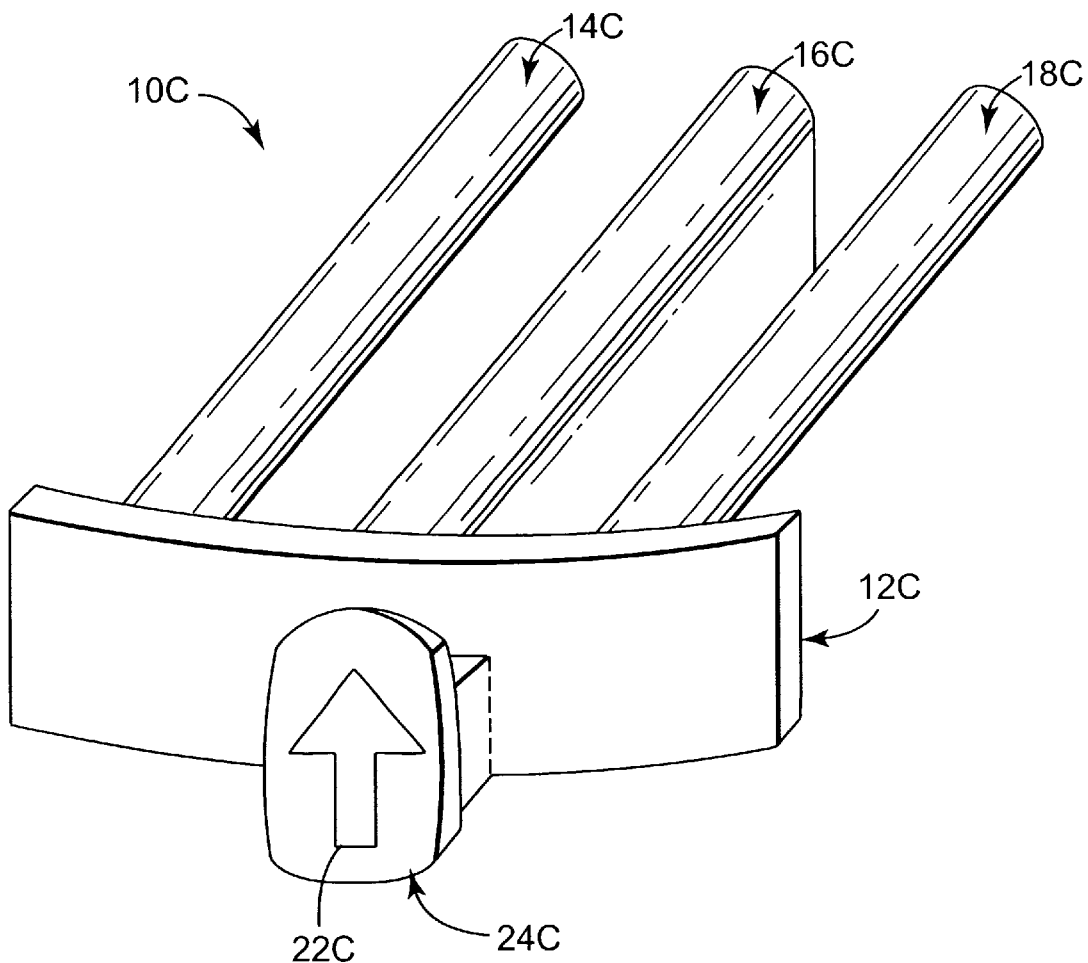
FIG. 4b shows a perspective view of an alternate embodiment of the tensioning device of the present invention having a grasping member disposing a directional indicator thereon positioned on the base member.

FIGS. 4a and 4b show additional embodiments of the present invention. Tension control article 10B has tensioning members 14B, 16B and 18B, and base member 12B. Tension control article 10C has tensioning members 14C, 16C and 18C, and base member 12C. As shown in FIG. 4b, the device 10C may include a grasping member 24C disposed on or attachable to the base member 12C. In FIG. 4a, the grasping member 24B is integral with the base member and comprises an arcuate discontinuity in the base member 12B. Optionally, the free (unattached) ends of tensioning members 14, 16 and 18 could include an enlarged portion or ledge that retains the sling material or sutures in place.

The grasping member 24C aids the user in applying, positioning, and removing the device 10C from the anatomical support material 20C. FIG. 4b shows the grasping member 24C further comprising a directional indicator 22C positioned thereon, thereby aiding the user in applying the device 10C. In an alternative embodiment of the present invention, a detachable grasping member 24C is contemplated.

Figure 5A:
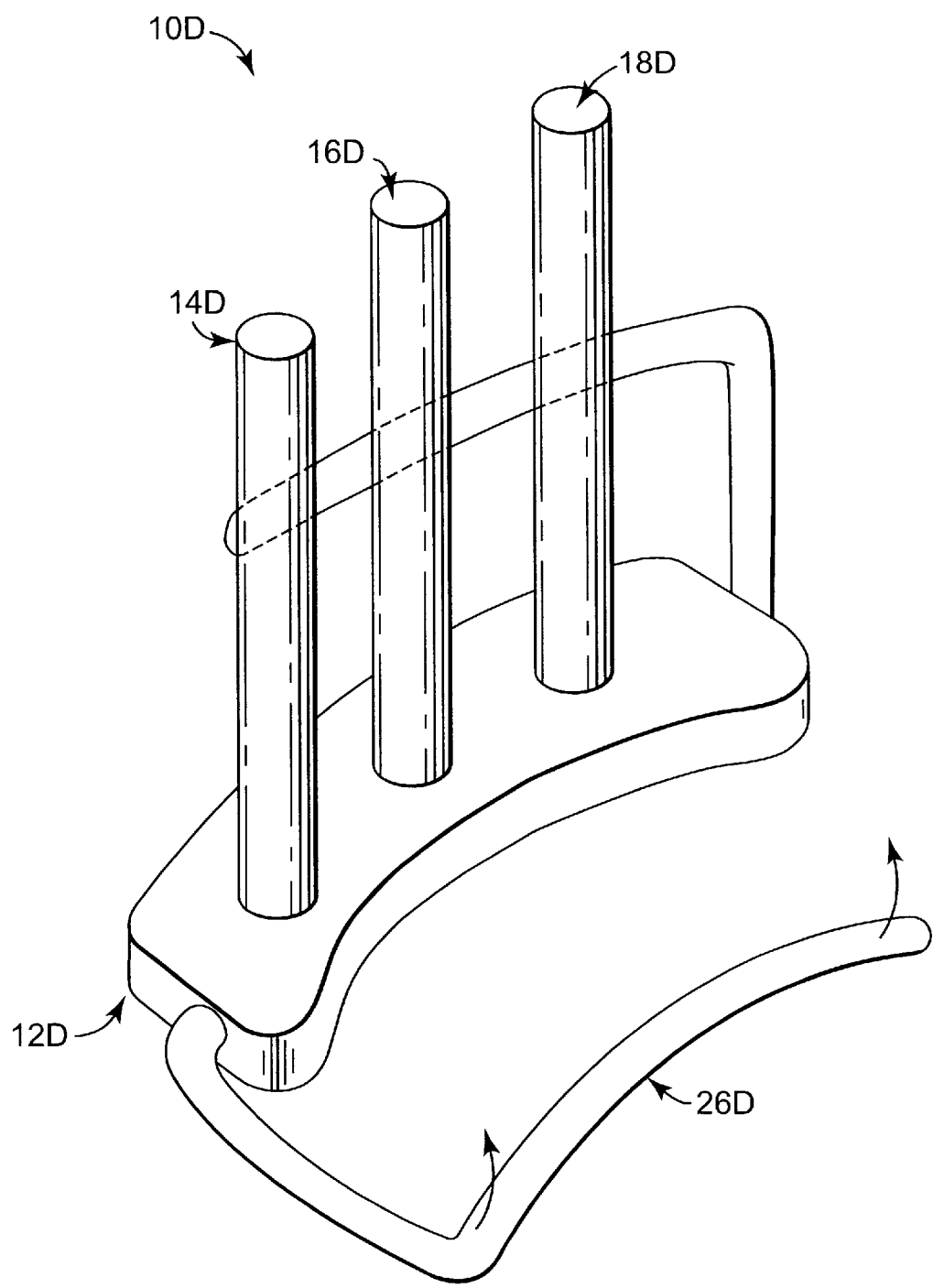
FIG. 5a shows a perspective view of another embodiment of tensioning device of the present invention having a locking member positioned thereon.
Figure 5B:
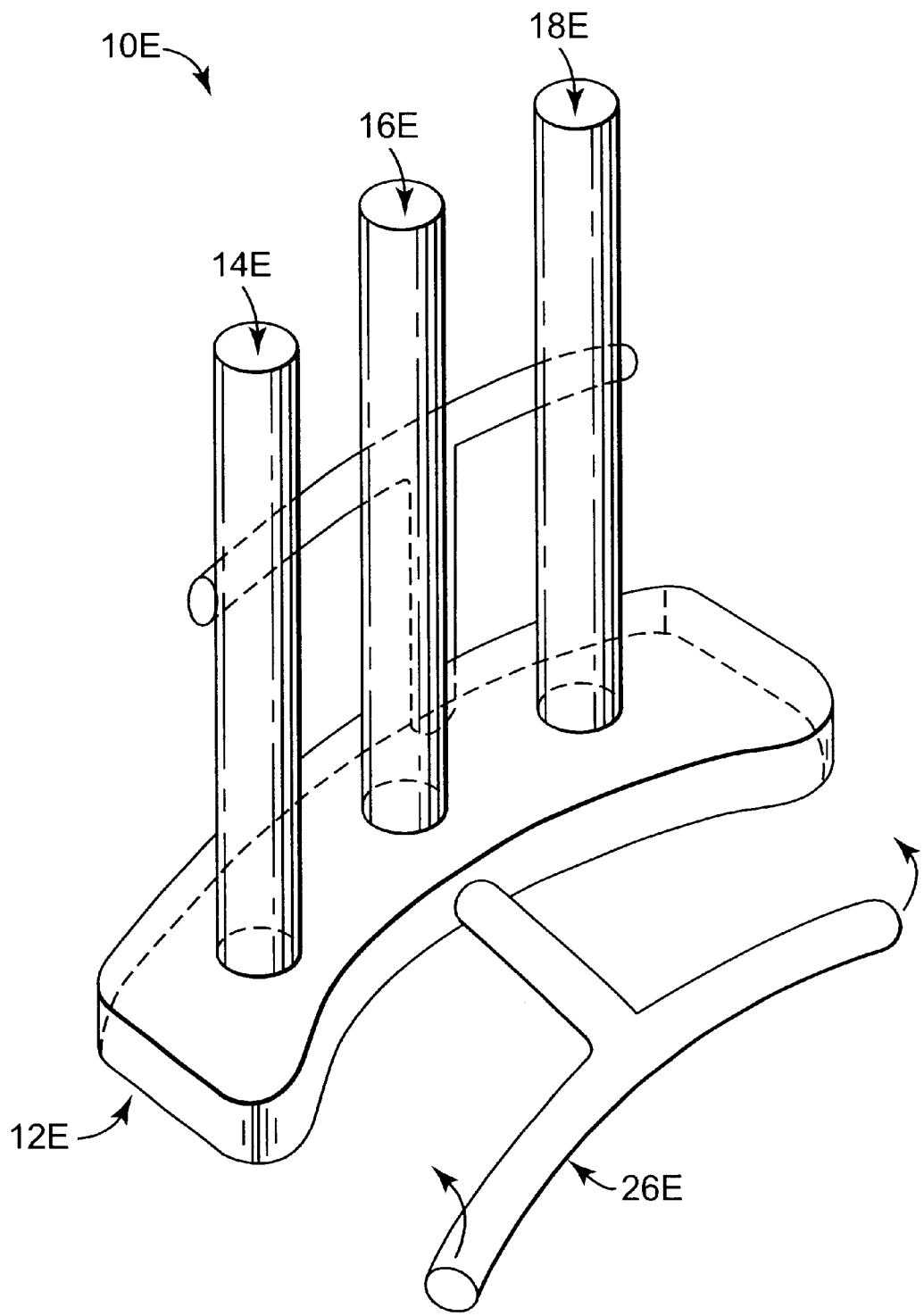
FIG. 5b shows a perspective view of an alternate embodiment of the tensioning device of the present invention having another embodiment of locking member positioned thereon.

Additional embodiments of the present invention are shown in FIGS. 5a and 5b. Tension control article 10D has tensioning members 14D, 16D and 18D, and base member 12D. Tension control article 10E has tensioning members 14E, 16E and 18E, and base member 12E. Base member 12D of the device 10D includes at least one material locking member 26D. The locking member 26D has an open position permitting the movement of anatomical support material 20 (see FIG. 2a) between the tensioning members 14D, 16D, and 18D, respectively, and a closed position restricting the movement of the anatomical support material 20 relative to the tension control article 10D. The at least one locking member may be manufactured from a plurality of materials having sufficient structural rigidity to prevent material movement, thereby preventing accidental or unintentional adjustment of the tension applied by the anatomical support material. The locking member 26E of FIG. 5b is located on the sides of the base portion 12E, as opposed to the ends (see FIG. 5a).

In another embodiment, the article of the present invention may include a spring biased locking member that is biased toward the closed position. In the closed position, the locking position retains a portion of the sling 20 in a pre-tensioned, elastically deformed condition. Placing the pretensioned sling and associated article in the patient and then subsequently removing the association between the article and the pre-tensioned sling can result in an increase in the tension encountered by a target anatomical structure such a urethra.

The tensioning members 14, 16, and 18 (and those to which a letter suffix has been added herein) may be manufactured from a plurality of materials. For example, the tensioning members 14, 16, and 18 may be manufactured from a flexible material, thereby providing a dynamic tensioning device capable of absorbing temporary variations in supportive loading. If desired, in an alternative embodiment the tensioning members 14, 16, and 18 may be manufactured from a rigid material, permitting the operator to forcibly remove a tensioning member if desired, thereby resulting in decreased support tension applied by the anatomical support material. In an alternate embodiment, the tensioning member may be manufactured from a pliable material, thereby permitting the user to easily position and apply the device 10.

The spacing and number of tensioning members may be adapted to adjust the tension of the anatomical support material disposed on the device 10. For example, a greater number of tensioning members would provide a more tortuous pathway, resulting in greater anatomical support tension or spacing adjustment. The exterior of the tensioning members are preferably smooth. In another embodiment of the present invention, the exterior of at least one of the plurality of tensioning members may be textured to increase anatomical support material retention, or to increase stability within the body if the tension control article is permanently implanted, or to promote tissue ingrowth.

Figure 6:
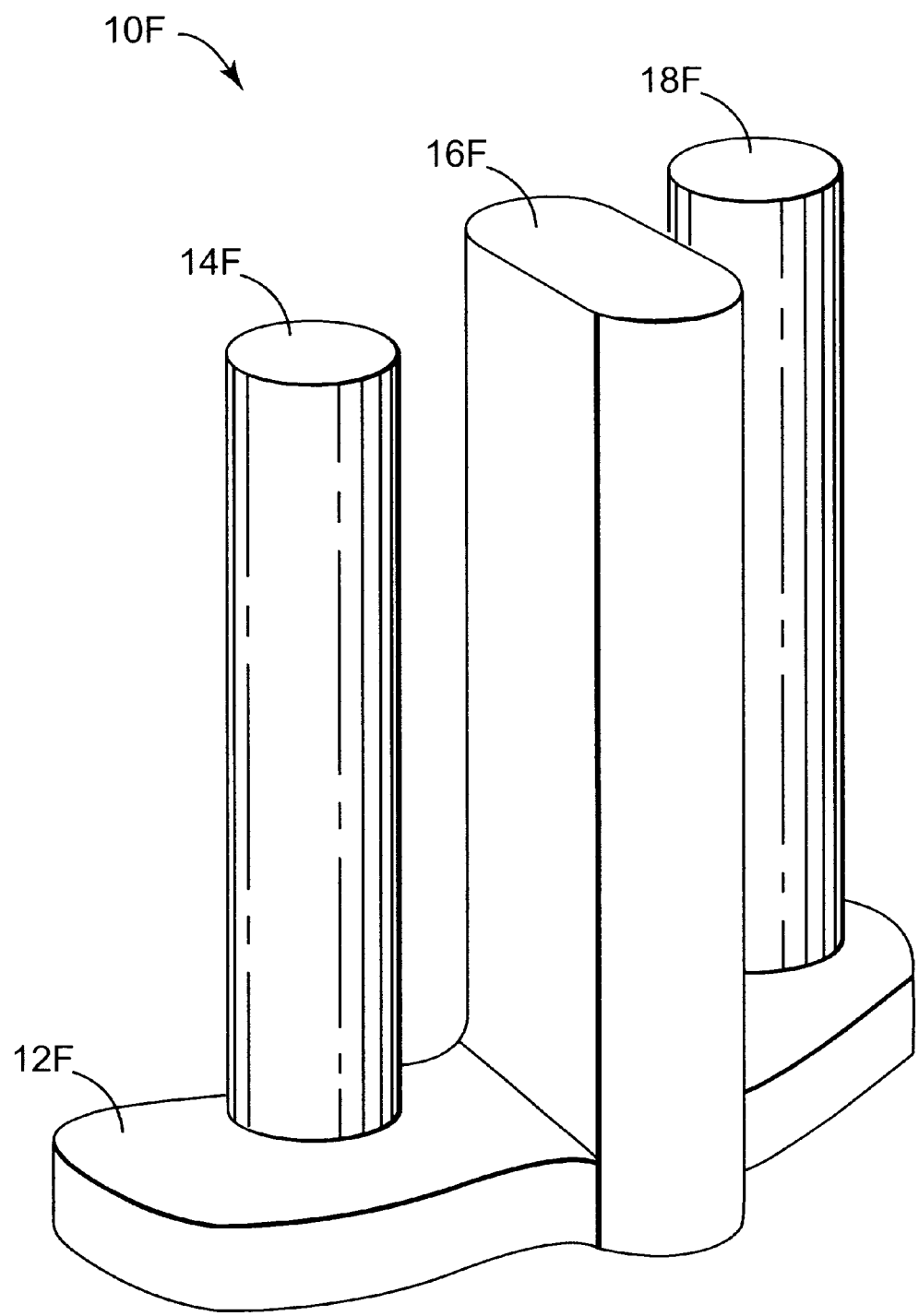
FIG. 6 shows a perspective view of an alternate embodiment of the tension device of the present invention wherein at least one tensioning member is oval.

FIG. 6 shows another embodiment of tension control article 10F including tensioning components 14F, 16F, and 18F. In FIG. 6, tensioning member 16F is oval. The tensioning members 14F, 16F, and 18F may be formed in a plurality of shapes and combinations thereof, including, without limitation, triangular, rectangular, oval, hexagonal, octagonal and diamond.

Figure 7:
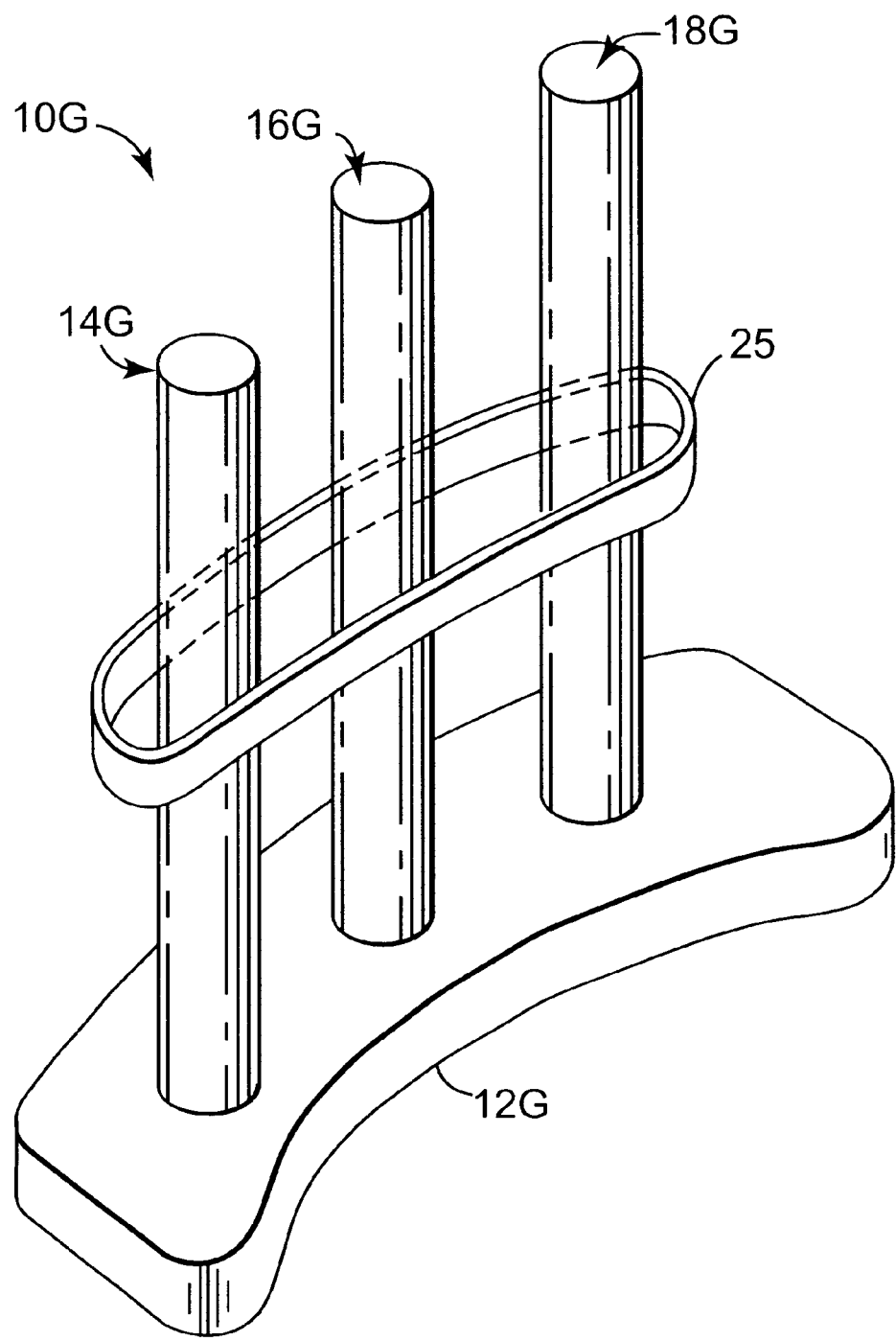
FIG. 7 is another embodiment of tensioning device according to the present invention that includes a securement member.
Figure 8A:
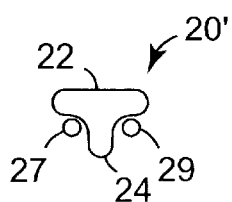
Figure 8B:
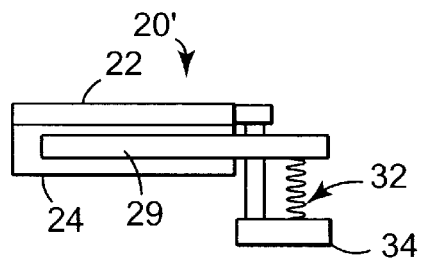
Figure 8C:
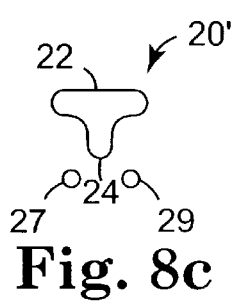
Figure 8D:
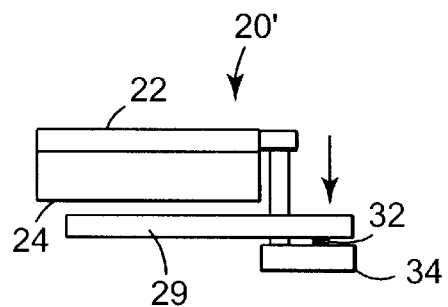
Figure 9A:
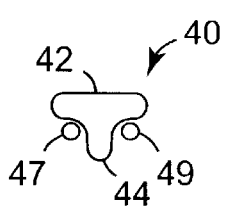
Figure 9B:
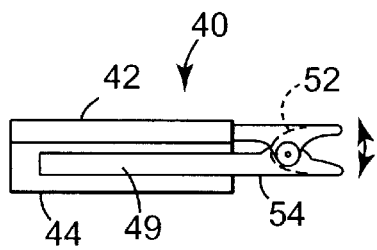
Figure 9C:
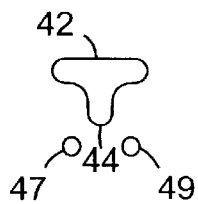
Figure 9D:
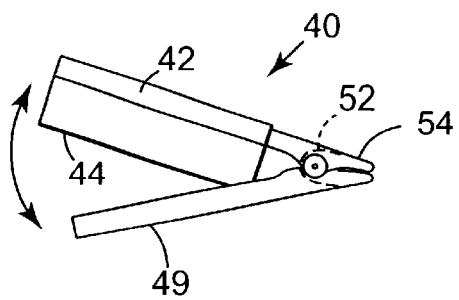

FIG. 7 illustrates another embodiment of tension control article 10G. Tension control article 10G has tensioning members 14G, 16G and 18G, and base member 12G. A band 25 may also be used in conjunction with tension control article 10G to retain the association between the sling 20 and tension control article 10G. The band 25 is placed on the tension control article 10G after the sling is associated with the tension control article 10G so that the band 25 prevents or blocks separation of the tension control article 10G from the support material 20.

FIGS. 8a–8d show another embodiment of tension control article 20' according to the present invention. The tension control article 20' comprises a base portion 22 with integral tensioning member 24, handle 34, and movable tensioning members 27 and 29.

The tension control article 20' is movable between an open position (FIGS. 8c and 8d) with the tensioning members 27 and 29 spaced from base portion 22 so that the tension control article 20' may readily receive a sling, and a closed position (FIGS. 8a and 8b) with the tensioning members 27,29 closer to the base portion 22 than in the open position.

A spring 32 biases the tension control article 20' toward the closed position. Manual pressure on handle 34 moves the tension control article from the closed toward the open position. The handle 34 is preferably designed so that major surfaces of the base portion 22 and tensioning members 27,29 remain substantially parallel between the open and closed positions. Substantial parallel movement resists binding or wrinkling of the sling when the tension members 27 and 29 clamp onto the sling.

FIGS. 9a–9d show another embodiment of tension control article 40 according to the present invention. The tension control article 40 comprises a base portion 42 with integral tensioning member 44, handle 54, and movable tensioning members 47 and 49.

The tension control article 40 is movable between an open position (FIGS. 9c and 9d) with the tensioning members 47 and 49 spaced from base portion 42 so that the tension control article 40 may readily receive a sling, and a closed position (FIGS. 9a and 9b) with the tensioning members 47,49 closer to the base portion 42 than in the open position.

A spring 52 biases the tension control article 40 toward the closed position. Manual pressure on handle 54 moves the tension control article from the closed toward the open position. The movement between the open and closed positions is pivotal movement about a point on or substantially adjacent handle 54.

FIGS. 10a–10d show another embodiment of tension control article 60 according to the present invention. The tension control article 60 comprises a base portion 62 with integral tensioning member 64, handle 76, and movable tensioning members 67 and 69.

The tension control article 60 is movable between an open position (FIGS. 10c and 10d) with the tensioning members 67 and 69 spaced from base portion 62 so that the tension control article 60 may readily receive a sling, and a closed position (FIGS. 10a and 10b) with the tensioning members 67,69 closer to the base portion 62 than in the open position.

A spring 72 biases the tension control article 60 toward the closed position. Manual pressure on handle 76 moves the tension control article from the closed toward the open position. The tension control article includes a hinge structure 74 that is preferably designed so that major surfaces of the base portion 62 and tensioning members 67,69 remain substantially parallel during movement between the open and closed positions. Parallel movement between these structures is believed to avoid sling material extruding out of the open end of the tension control article 60 as the sling is being associated with the tension control article 60.

Figure 11A:
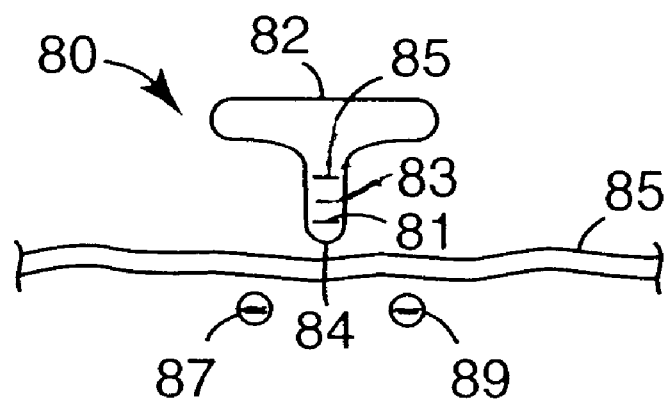
FIG. 11a is an end view of another embodiment of tensioning article and sling according to the present invention with tensioning indicia located thereon, which tensioning article is shown in an open position.
Figure 11B:
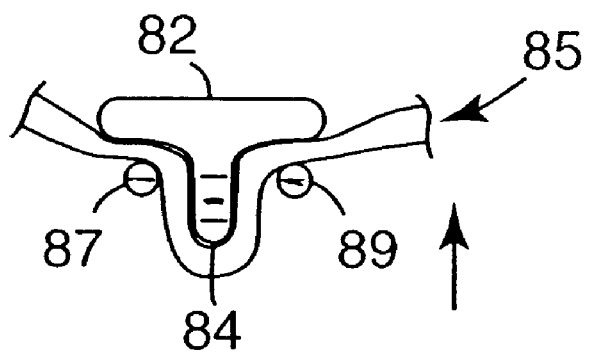
FIG. 11b illustrates the assembly of FIG. 11a in a closed position.

FIGS. 11a–11b show another embodiment of tension control article 80. The tension control article comprises a base portion 82 with integral tensioning member 84, a handle, and movable tensioning members 87 and 89. The tension control article 80 is movable between an open position (FIG. 11a) with the tensioning members 87 and 89 spaced from base portion 82 so that the tension control article 80 may readily receive a sling 85', and a closed position (FIGS. 11b) with the tensioning members 87,89 closer to the base portion 82 than in the open position.

The tension control article 80 includes tension level indicators 81, 83 and 85 on tensioning member 84. The indicators 81, 83 and 85 may comprise printing, molded in indicia or other forms of indicia. Members 87 and 89 may also include indicia thereon. The position of the indicators 81, 83 and 85 relative to the indicia on members 87 and 89 provide an indication of the tension provided by the tension control article 80.

Preferably, the tension control article 80 includes structure that releasably indexes the tension members 87,89 between locations adjacent indicators 81, 83 and 85. A releasable detent and groove associated with a hinge provides suitable structure. Locations 81, 83 and 85 correspond to predetermined positions between the open (FIG. 11a) and fully closed (FIG. 11b) positions. Generally, the closer the tension members 87 and 89 are to the base portion 82, the more slack will be provided in sling 85' when the tension control article 80 is removed.

Figure 12:
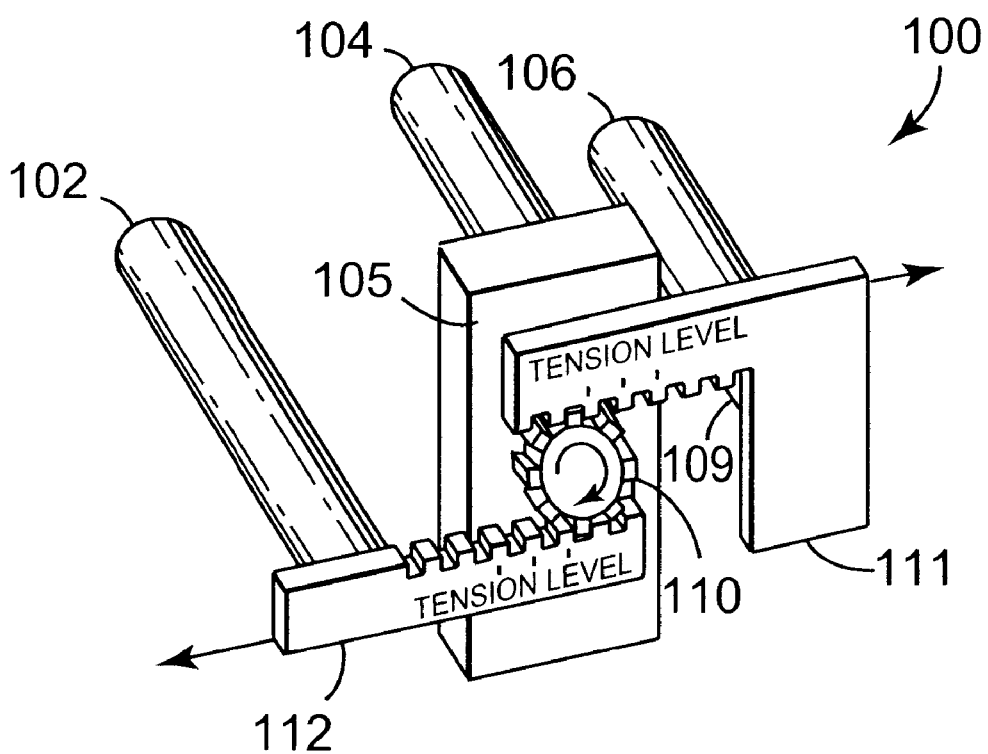
FIG. 12 is a perspective view of another embodiment according to the present invention which embodiment includes an adjustment feature.

FIG. 12 illustrates another embodiment of tension control article 100. The tension control article 100 comprises tensioning members 102, 104 and 106, base member 105, and adjustment member 110. The tensioning members 102 and 106 are located on arms 112 and 111 that are movable relative to tensioning member 104. By rotating a geared wheel 110 that engages gears on arms 111 and 112, the tensioning members 102 and 106 may be moved away from or closer to tensioning member 104. Indicia 109 may be printed on or embossed on the arms 111 and 112 to provide an indication of the preselected tension provided by the tension control article 100. Adjustable tension control article 100 allows the surgeon to preselect a tension to account for the vagaries in human anatomy sizes, surgical procedure requirements or personal preference.

Figure 13:
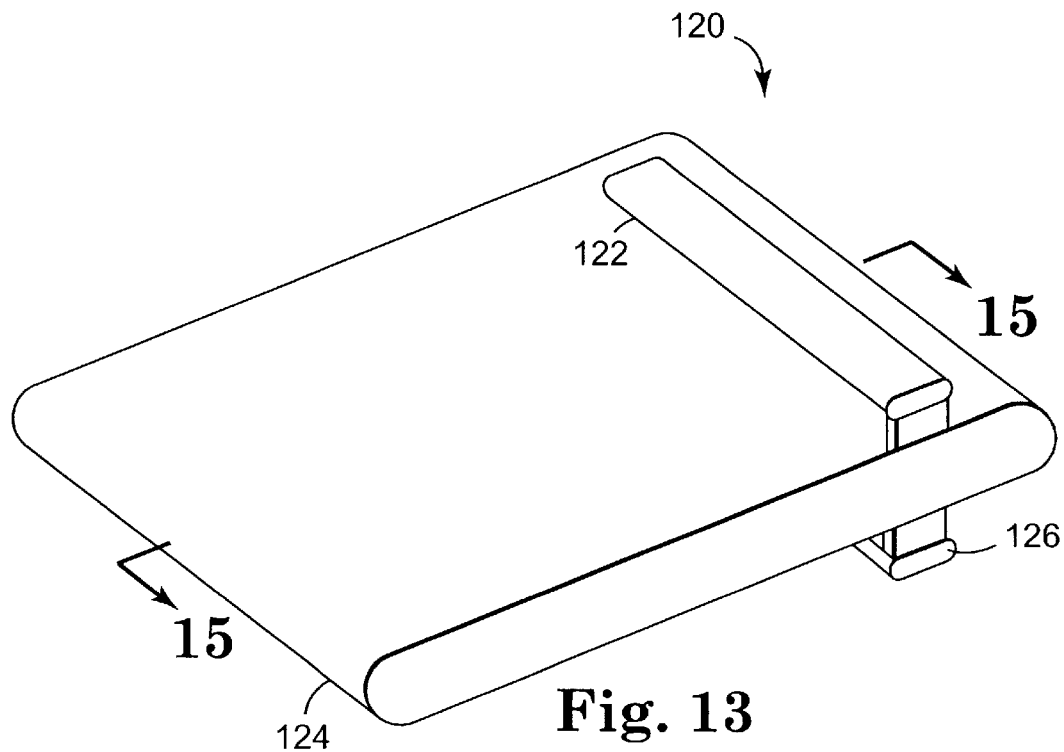
FIG. 13 is a perspective view of another embodiment of tensioning device according to the present invention.
Figure 14:
FIG. 14 is an end view of the article of FIG. 13 with a sling threaded through the article in a first orientation.
Figure 15:
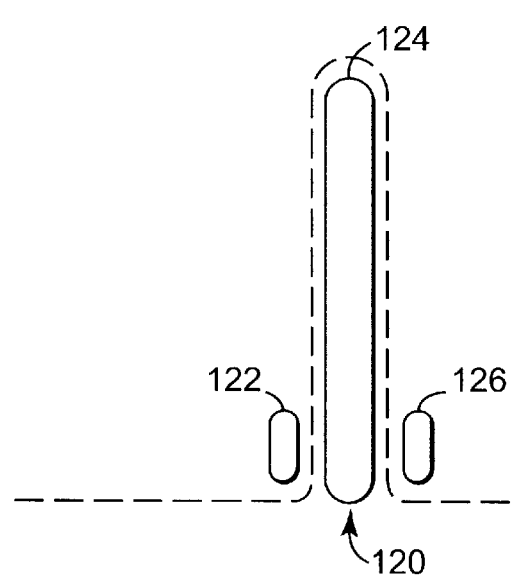
FIG. 15 is another end view of the article of FIG. 13 with a sling threaded through the article in a second orientation.

FIGS. 13–15 illustrate another embodiment of tension control article 120 according to the present invention. The tension control article 120 includes major tensioning member 124 and minor retention members 122 and 126. FIGS. 14 and 15 illustrate different tortuous paths associated with tension control article 120. Sling 127 is associated with article 120 by being threaded within tension control article 120 along one of the tortuous paths. The tortuous path of FIG. 14 is shorter than the tortuous path of FIG. 15. Generally, the longer the tortuous path, the more slack will be provided in the sling 127 when the tension control article 120 is removed. Also, the longer the tortuous path, the more slack is taken up in an implanted sling when the article 120 is applied to the sling.

Figure 16A:
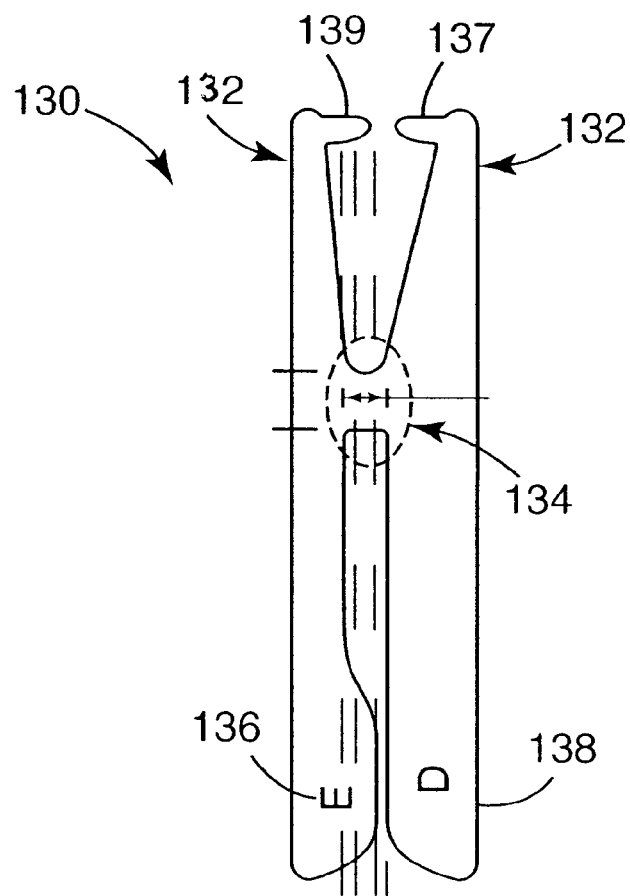
FIG. 16a is a side view of another embodiment of surgical article according to the present invention.
Figure 16B:
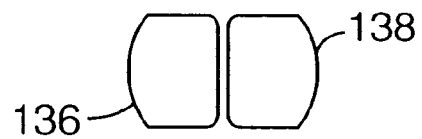
FIG. 16b is an end view of the article of FIG. 16.

FIGS. 16a and 16b illustrate another embodiment of tension control article 130 according to the present invention. The tension control article 130 includes spacer jaws 136 and 138, hinge 134, handles 132 and over opening stops 137 and 139. The tension control article 130 is preferably a unitary structure with an inherent bias of the jaws toward a closed or clamped position.

The hinge 134 may comprise an integral or living hinge that biases the jaws 136 and 138 toward a closed position. In use, manual pressure is applied to handles 132 to open the jaws. A sling is placed in the open jaws and the handle is released. Upon release, the sling is clamped between the jaws 136 and 138. The sling is then placed next to the urethra with jaw 136 located between the sling and the urethra. The jaw 136 is sized and shaped to provide a predetermined distance between the urethra and sling. The tension control article 130 is then removed. The predetermined distance or size of jaw 146 assists the surgeon in providing a consistent, uniform and repeatable amount of looseness in a sling.

Figure 17A:
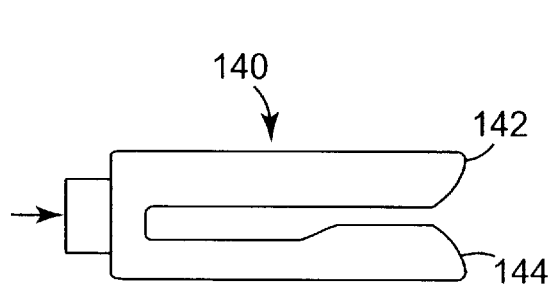
FIG. 17a is a side view of another embodiment of tensioning device according to the present invention.
Figure 17B:
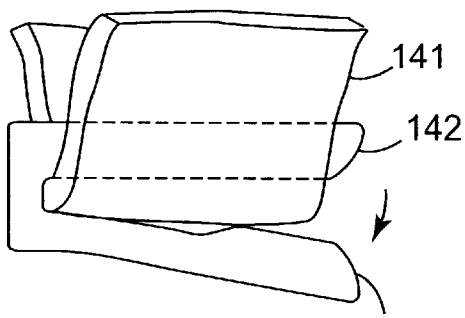
FIG. 17b is a side view of the tensioning device of FIG. 17a with a sling inserted therebetween.

Another embodiment of tension control article 140 is shown in FIGS. 17a and 17b. Tension control article 140 includes jaws 142 and 144. A sling 141 is shown placed within the jaws in FIG. 17b. Optionally, jaw 142 may be constructed to be a different size than jaw 144 to afford two different spacing options for the surgeon.

Figure 18A:
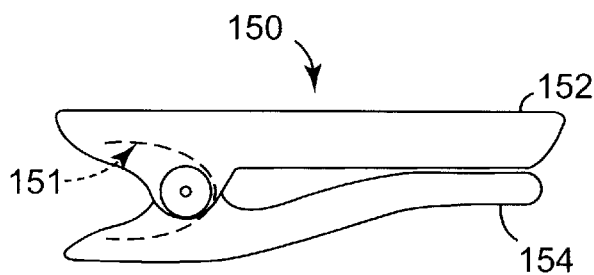
FIG. 18a is a side view of another embodiment of tensioning device according to the present invention shown in a closed position.
Figure 18A:
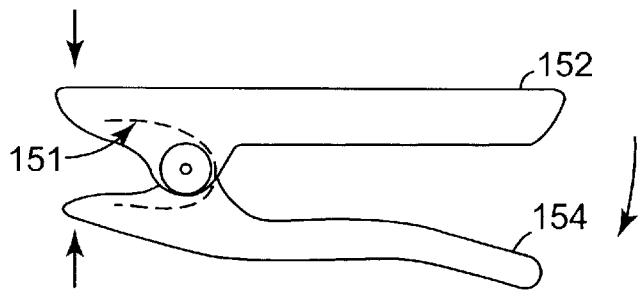
Figure 18C:
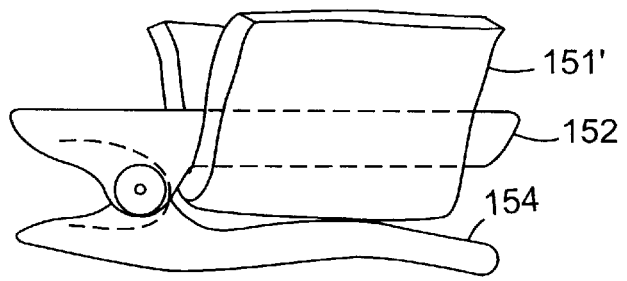
FIG. 18c is a view of the tensioning device of FIGS. 18a and 18b with a sling placed therein.

FIGS. 18a through 18c show another embodiment of tension control article 150 according to the present invention. The tension control article 150 includes jaws 152 and 154, a hinge and a spring 151 for biasing jaws 152 and 154 toward a closed position. Sling 151 ' is shown placed between jaws 152 and 154 in FIG. 18C.

The device according to the invention may be easily tailored to provide increased or decreased urethral support. Optionally, the tension control article may allow the surgeon to remove, or break the tensioning members during the surgical procedure or during a post operative period.

Method

In another aspect, the present invention comprises a method of changing tension of an implantable article using an article according to the present invention. The article may be implanted in the body during a surgical procedure. Alternatively it may be removed prior to the end of a surgical procedure. The article of the present invention may be modified in a subsequent surgical procedure or by substantially non-invasive means.

Figure 19:
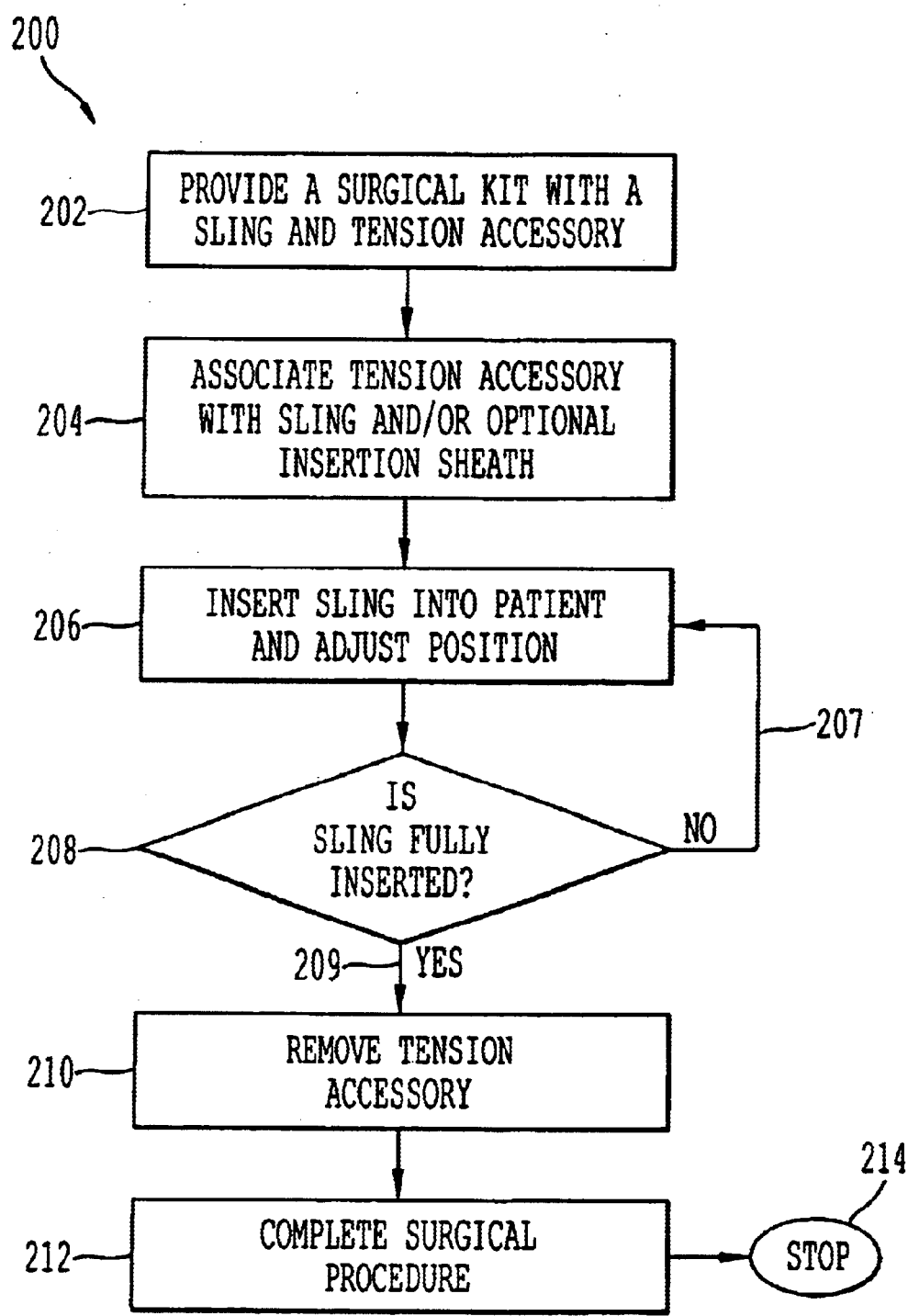
FIG. 19 is a flow chart showing a surgical procedure according to the present invention.
Figure 20:
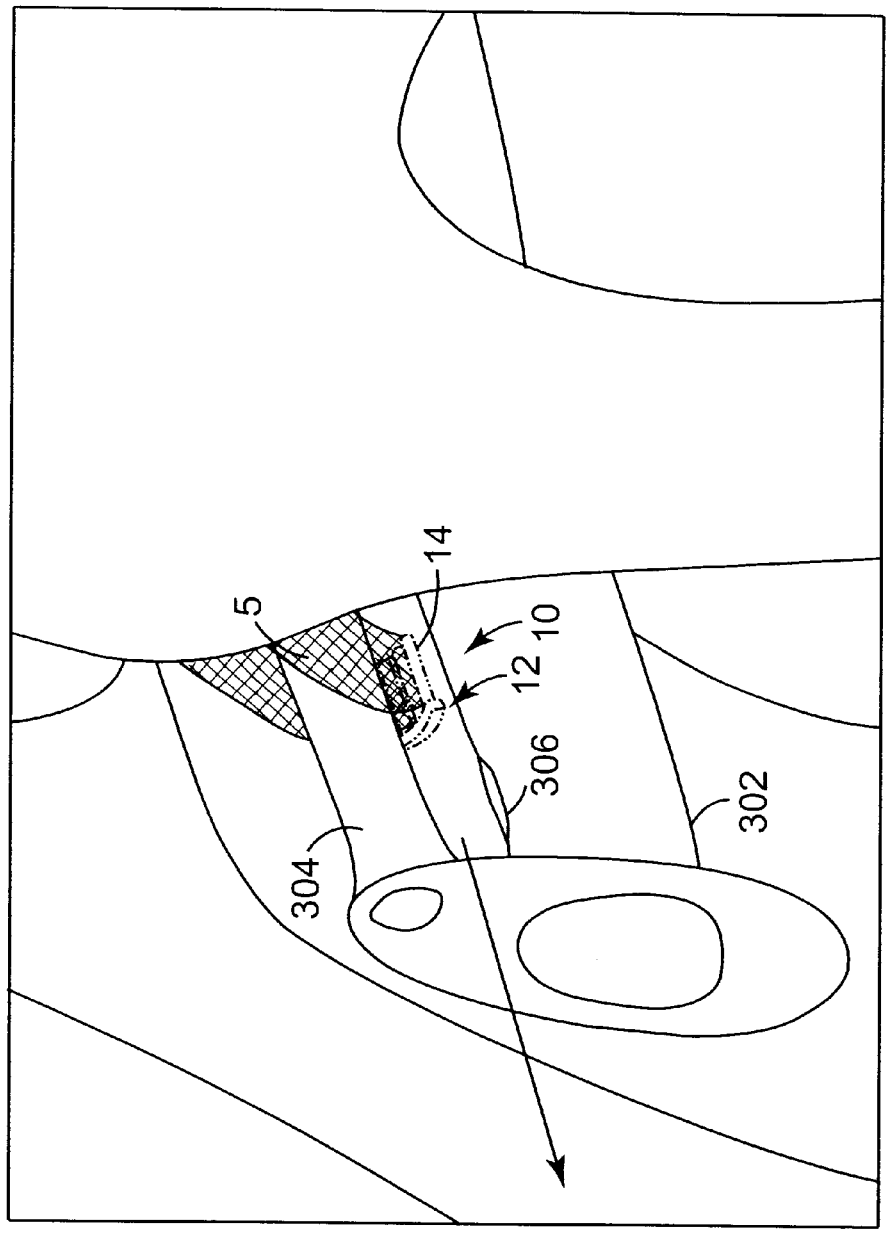
FIG. 20 is a schematic view of a tensioning article, sling and selected portions of the anatomy of a patient, which view illustrates removal of the tensioning article after it sets sling tension.
Figure 20:
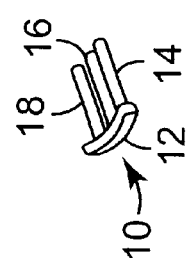

FIGS. 19 and 20 illustrate a method where the surgical article is removed prior to the end of the surgical procedure. FIG. 19 is a flowchart illustrating an embodiment of method 200 according to the present invention.

Step 202 provides a tension control article (tension accessory) and a sling. Preferably, the tension control article (e.g. 10) may be part of a surgical kit. The kit may be a surgical kit having tools for treating incontinence, such a sling kit. Alternatively, the tension control article, sling and the rest of the surgical articles may be independently provided to the surgeon. The latter case is desirable when the elements of the kit have drastically different shelf lives or storage condition requirements (e.g. refrigeration).

Step 204 associates the tension accessory (the tension control article) with the sling. Optionally, the manufacturer can conduct this step so that a sling/tension control article preassembly is provided to the surgeon in the kit. Alternatively, this step may be conducted by the surgeon or other healthcare professional prior to implanting the sling, especially if the tension control article provides a plurality of different tension options.

Figure 23:
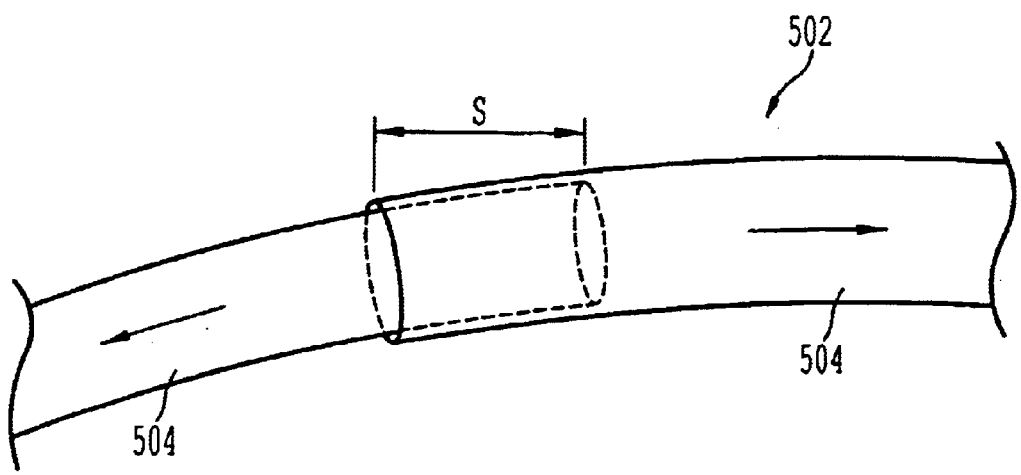
FIG. 23 is a perspective view of an embodiment of a removable sheath according to the present invention.

Using tension control article 10 as an example, to associate the article 10 with a sling, the operator threads the sling along one of the tortuous paths provided by the article 10. It is noted that, if the sling includes a surrounding, removable plastic sheath, the sling/sheath combination may be threaded along the tortuous path. FIG. 23 illustrates a removable plastic sheath 502. As shown in FIG. 23, the sheath 502 preferably comprises two elongate sections 504. Alternatively, other configurations of the sheath 502 are within the scope of the present invention. In particular, the sheath may be unitary as opposed to telescoping with perforations, holes, scores or tear lines designed to allow separation and removal of the sheath 502.

In step 206, the sling is inserted in the body and adjusted to a predetermined position. For example, some sling procedures call for a tension free sling. For such a procedure, the sling/tension control article combination can be situated in a fully inserted position such that the sling and/or the tension control article are just adjacent or even slightly touching the urethra.

FIG. 20 schematically illustrates article 10 in a fully inserted position with solid lines. The article 10 is just adjacent urethra 304. Vaginal incision 306, vagina 302, and sling S are also shown. In step 208 (FIG. 19), the surgeon verifies that the sling/tension control article combination are in this fully inserted position. If not, the surgeon continues to adjust 207 the sling. If the combination is fully inserted, then the surgeon verifies the fully inserted position 209. Once the fully inserted position is verified, the surgeon may remove the tension control article in step 210. This removal step is illustrated with an arrow and dotted lines in FIG. 20. Step 210 may be conducted before or after any optional insertion sheath is removed from the sling, but it preferably occurs after any such optional insertion sheath is removed.

Changing the tension of the sling S at a location substantially adjacent the urethra 304 is more effective than attempting to modify the tension of a sling at a location remote from the urethra. This is particularly the case where a synthetic sling (a polypropylene sling with holes) and insertion sheath are used as, once the insertion sheath is removed, adjustment of the entire length of the sling is particularly difficult or problematic due to the interaction between tissue and the sling.

Figure 21:
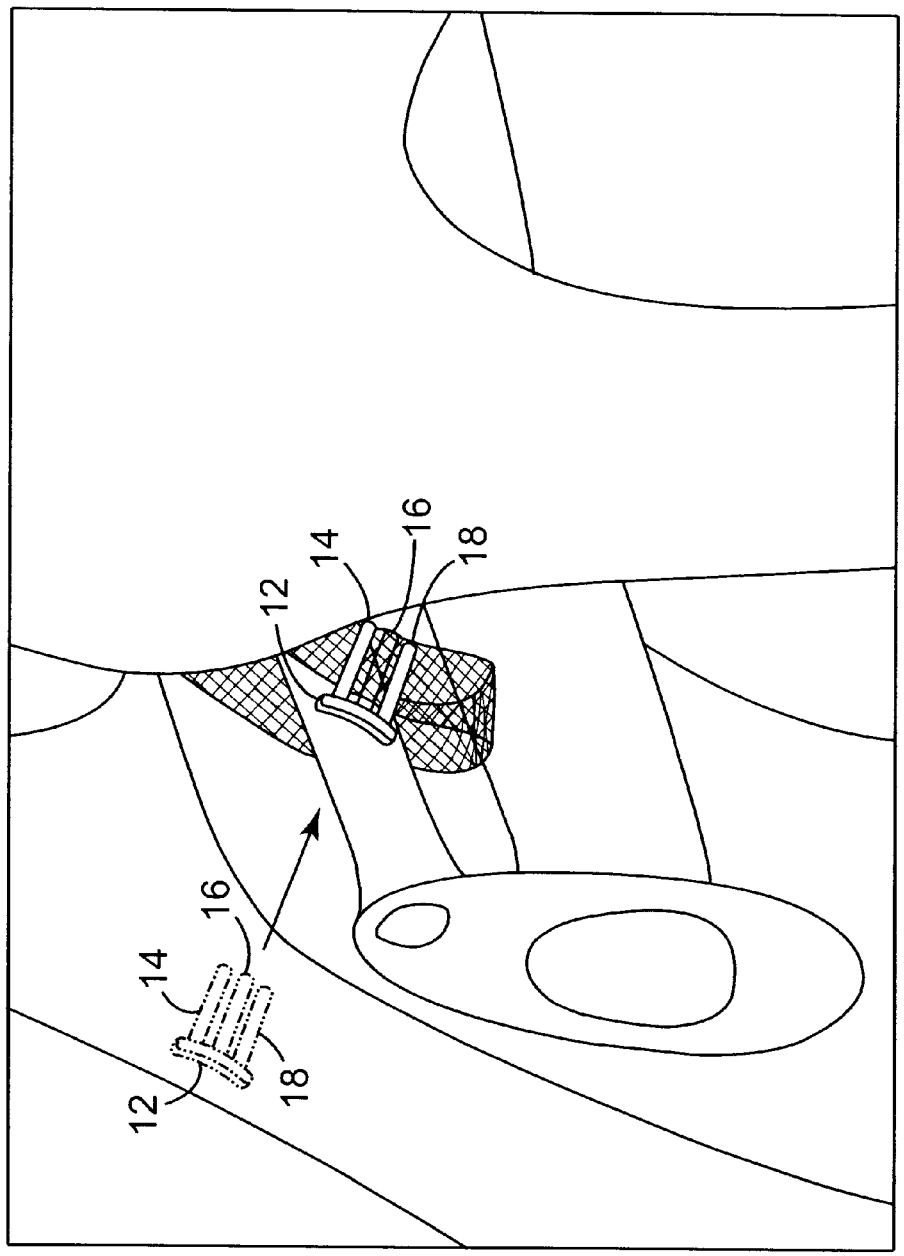
FIG. 21 is a schematic view of a tensioning article, sling and selected portions of the anatomy of a patient, which view illustrates implantation of the tensioning article to increase the tension of the sling.

FIG. 21 illustrates another embodiment of method according to the present invention. In this embodiment, the sling is excessively loose. Article 10 is placed on the sling (see the arrow and solid lines) to take up excessive slack in the sling. In this instance, article 10 is preferably left in the body after the surgical procedure. Preferably, by positioning the sling within the tortuous pathway formed by the plurality of tensioning members, article 10 effectively increases the path length traversed by the support material, thereby resulting in a reduction or elimination of slack from the support material and an increase in supportive tension unless and until the tension control article is removed. As shown in FIGS. 2a and 2b, multiple degrees of retentive force may be applied to anatomical support material by a device 10. For example, FIG. 2a shows one method of practice wherein the device 10 provides a tortuous pathway for a section of anatomical support material 20 disposed thereon. An alternative method of practice is shown in FIG. 2b, wherein an alternate tortuous pathway is created. FIG. 12 illustrates an article with a feature that allows the surgeon to adjust the tension provided by the clip. In preferred embodiments, the present invention permits the user to vary the supportive tension applied to the anatomical support material disposed therein by altering the tortuous pathway traversed by the anatomical support material.

Figure 22:
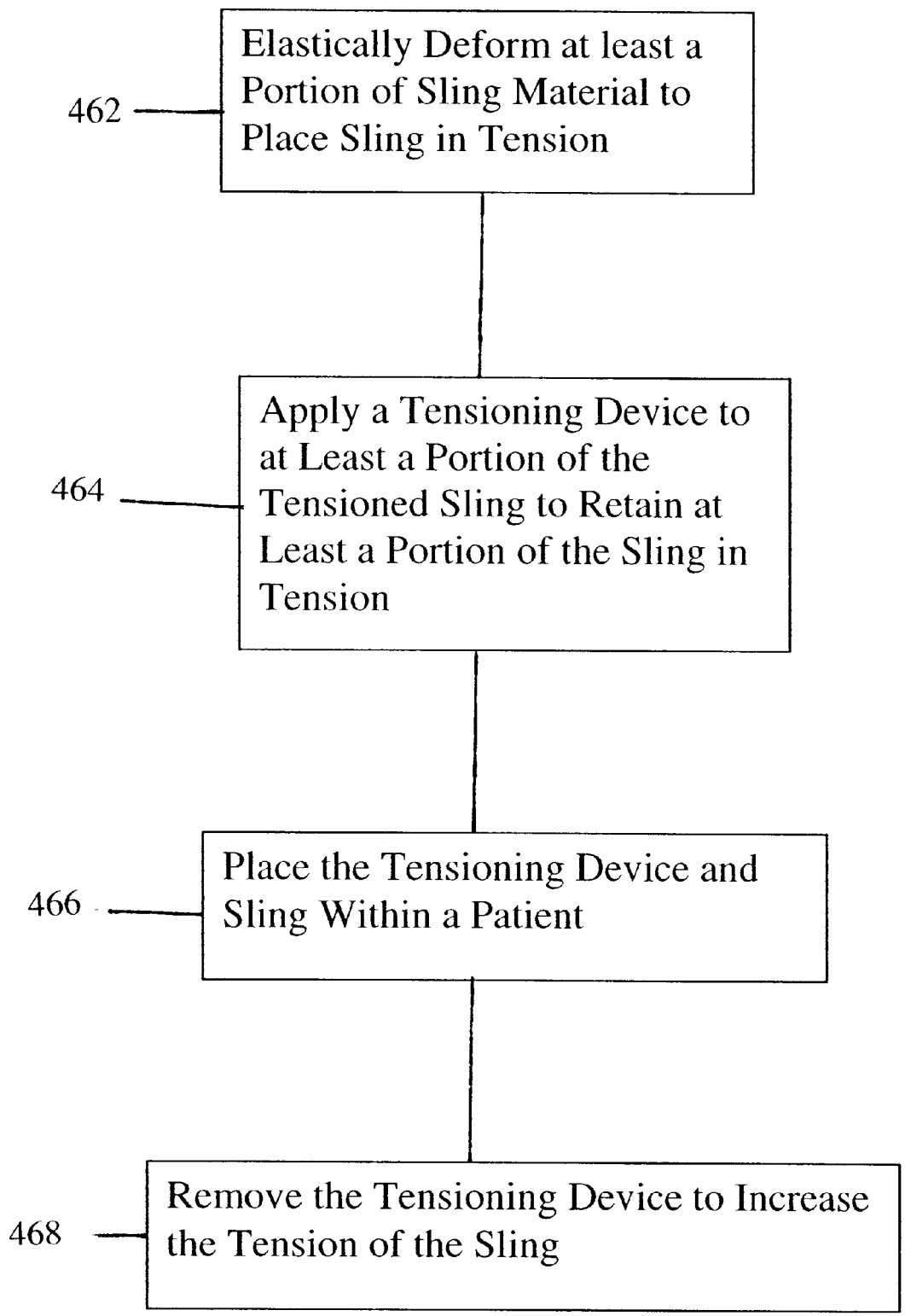
FIG. 22 is a flowchart showing an example of a method according to the present invention.

It is also noted that removal of an article from its association with the sling can be exploited to increase the tension of the sling on the urethra. FIG. 22 is a flow chart illustrating a method of increasing the tension of a sling by removing a tension control article from its association with the sling.

FIG. 22 illustrates a method of treating incontinence comprising the steps of: (i) providing a support material with at least a portion that is elastically deformable, (ii) elastically deforming at least a portion of the support material to tension the support material (see step 462); (iii) providing a tensioning article, (iv) applying the tensioning article to the tensioned support material to retain at least a portion of the support material in an elastically deformed condition (see step 464); (v) implanting the support material with applied tensioning article in a patient (466); and removing the tensioning article to increase the tension provided by the support material 468. The tension control article used in this method is preferably one with a locking member (FIG. 5a or 5b) or one that can clamp the sling between jaw members (e.g. FIGS. 10a–10b) so that the elastic deformation can be held in the sling material.

The tension control article may be provided in a kit or provided independent of other surgical articles. One or more articles may be used during a surgical procedure. The tension control article may be positioned on a portion of anatomical support material at the time of manufacture, immediately prior to, or following the surgical implantation of the anatomical support. For example, one surgical urethral stabilization procedure comprises attaching anchors to an internal structure, for example, the posterior or inferior pubic bone, and affixing a mesh sling to said anchors, thereby resulting in supportive force being applied to the urethra. The tension control article 10 may be applied to the anatomical support material according to FIG. 2a or 2b should the anatomical support fail to provide adequate support to the anatomical structure. Applying the tensioning device 10 to the anatomical support material increases the pathway between the attaching anchors traversed by the anatomical support and increases the support tension applied by the device. The practitioner may easily vary the amount of supportive tension by applying more or fewer anatomical support tension control articles. Alternatively, the amount of supportive tension applied by the anatomical support tensioning device may be varied by applying tensioning device having more or fewer tensioning members disposed thereon.

It is understood that the embodiments of the invention disclosed herein are illustrative of the principles of the invention. Other modifications may be employed which are within the scope of the invention; thus, by way of example but not of limitation, alternate base member shapes, alternative tensioning member shapes, and use with alternative anatomical support materials. Accordingly, the present invention is not limited to that precisely as shown and described in the present invention.

What is claimed is:

1. A method comprising the steps of:

providing a sling and tensioning article, associating the tensioning article with the sling, implanting the sling and associated tensioning article in a position substantially adjacent the urethra so that the tensioning article provides a uniform distance between the urethra and the sling, and then removing the tensioning article.

2. A method of providing a uniform distance between the urethra and a sling comprising:

providing a sling and tensioning article, associating the tensioning article with the sling, implanting the sling and associated tensioning article in a position substantially adjacent the urethra, and then removing the tensioning article, wherein the step of providing a sling and tensioning article includes the step of providing a removable insertion sheath surrounding the sling; and the step of associating the tensioning article with the sling includes the step of associating the sling and sheath combination with the tensioning article.

3. A method comprising the steps of:

providing a sling and tensioning article, associating the tensioning article with the sling, implanting the sling and associated tensioning article in a position touching the urethra so that the tensioning article provides a uniform distance between the urethra and the sling, and then removing the tensioning article.

4. A surgical kit comprising:

a sling for treating urinary incontinence, surgical articles for implanting the sling, and a tensioning article that is sized and shaped to be placed between the sling and the urethra of the patient and configured to provide uniform spacing between the sling and the uretha.

5. A method of treating incontinence comprising the steps of:

providing a support material with at least a portion that is elastically deformable, elastically deforming at least a portion of the support material to tension the support material;

providing a tensioning article, applying the tensioning article to the tensioning support material to retain at least a portion of the support material in an elastically deformed condition;

implanting the support material with applied tensioning article in a patient;

removing the tensioning article to increase the tension provided by the support material.

* * * * *